(12) United States Patent
Masada

(10) Patent No.: US 6,454,808 B1
(45) Date of Patent: Sep. 24, 2002

(54) FINGER JOINT PROSTHESIS

(75) Inventor: Kazuhiro Masada, Hyogo (JP)

(73) Assignee: M-E-System Inc., Tokyo (JP)

( * ) Notice: Subject to any disclaimer, the term of this patent is extended or adjusted under 35 U.S.C. 154(b) by 0 days.

(21) Appl. No.: 09/407,634

(22) Filed: Sep. 28, 1999

Related U.S. Application Data

(62) Division of application No. 09/015,032, filed on Jan. 28, 1998, now abandoned.

(51) Int. Cl.[7] ................................................. A61F 2/24
(52) U.S. Cl. ............................... 623/21.15; 623/21.13; 623/21.16
(58) Field of Search ......................... 623/21.15, 21.13, 623/21.16, 21.14, 21.11, 21.12

(56) References Cited

U.S. PATENT DOCUMENTS

| | | | | |
|---|---|---|---|---|
| 3,638,243 A | * | 2/1972 | Campbell et al. | 623/21 |
| 4,106,128 A | * | 8/1978 | Greenwald et al. | 623/21 |
| 5,047,059 A | * | 9/1991 | Saffar | 623/21 |
| 5,147,386 A | * | 9/1992 | Carignan et al. | 623/21 |
| 5,549,681 A | * | 8/1996 | Segmuller et al. | 623/18 |

FOREIGN PATENT DOCUMENTS

| | | | | |
|---|---|---|---|---|
| JP | | 405168656 | * 7/1993 | 623/21 |

* cited by examiner

*Primary Examiner*—Corrine McDermott
*Assistant Examiner*—Alvin Stewart
(74) *Attorney, Agent, or Firm*—Michael J. Striker

(57) ABSTRACT

A finger joint prosthesis for MP joint or PIP joint in which a socket has an opening at a portion thereof and a spherical face on an inner side thereof and is integrally formed with a stem on a side opposed to the opening, a head has a spherical portion fit to the spherical face via the opening and is integrally formed with a stem extending outwardly from the opening and a sheath for surrounding the stem of either of the socket and head is provided and the stem is movable slidably in an axial direction by adhering and fixing the sheath to a narrow cavity at a nearly disposed portion or a remotely disposed portion whereby the joint prosthesis is matched with motional characteristic of finger.

16 Claims, 19 Drawing Sheets

Fig. 1-A
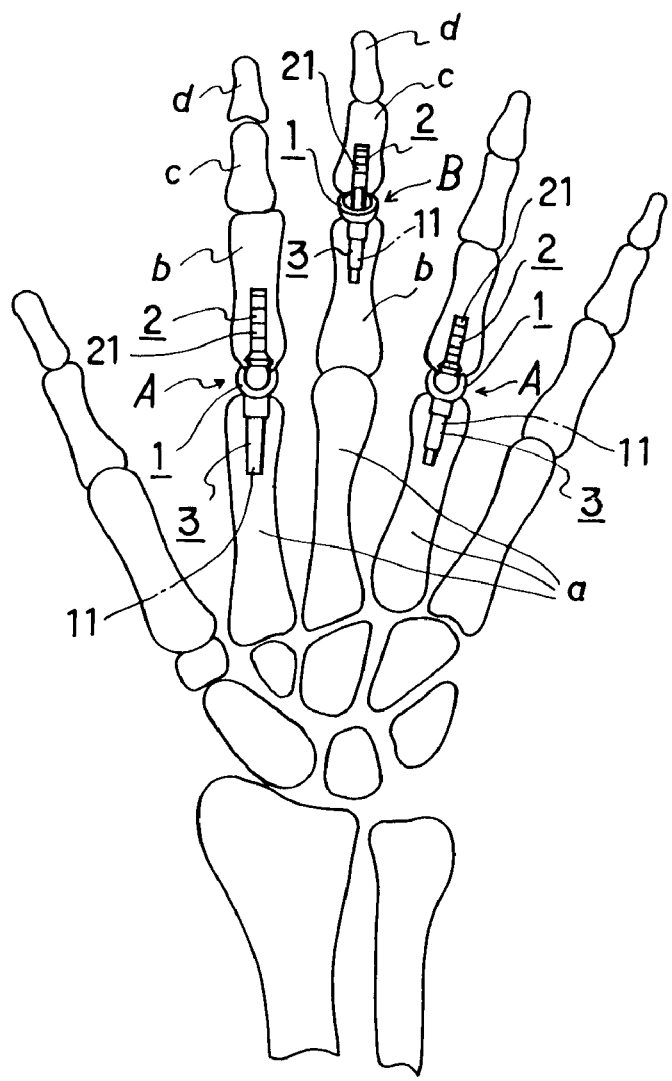
Fig. 2
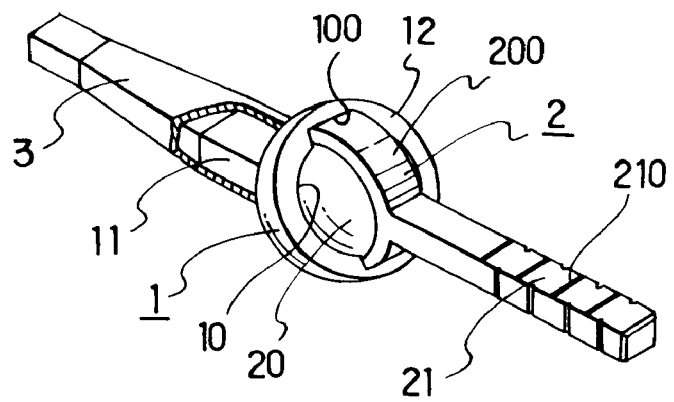

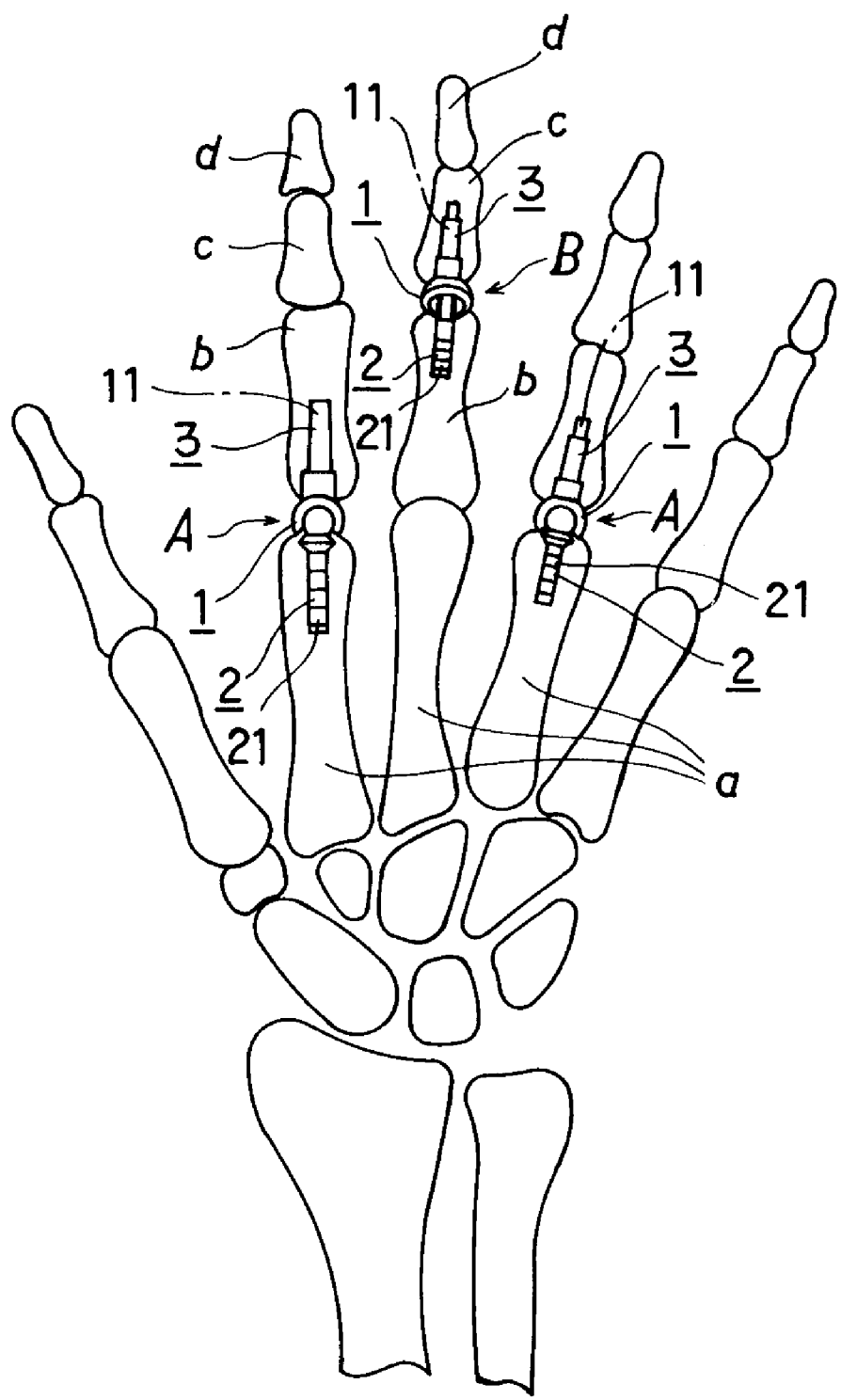
Fig. 1-B

Fig. 6
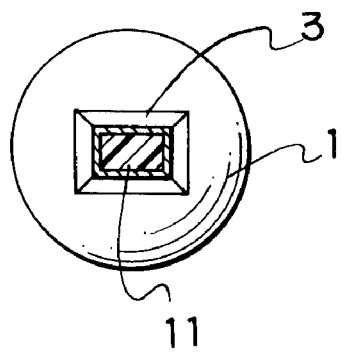
Fig. 7-A
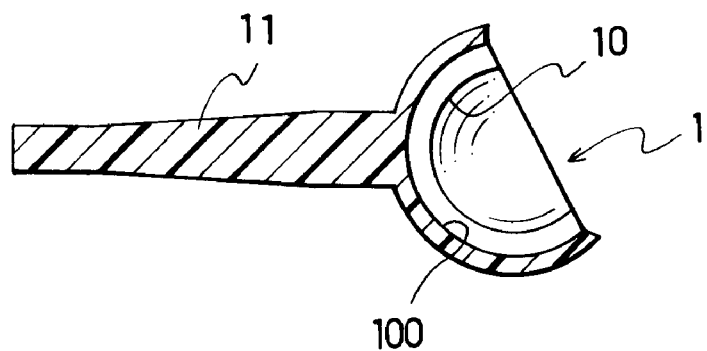
Fig. 7-B
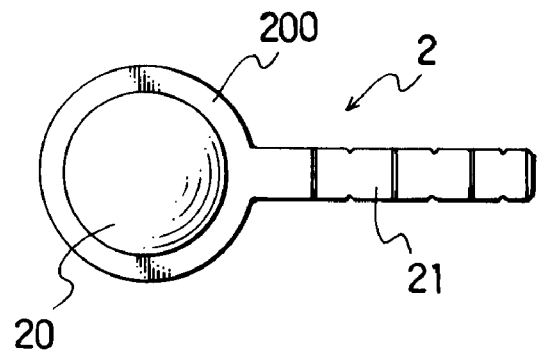
Fig. 7-C
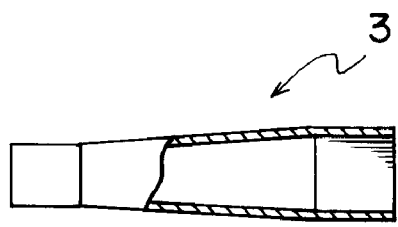

Fig. 11
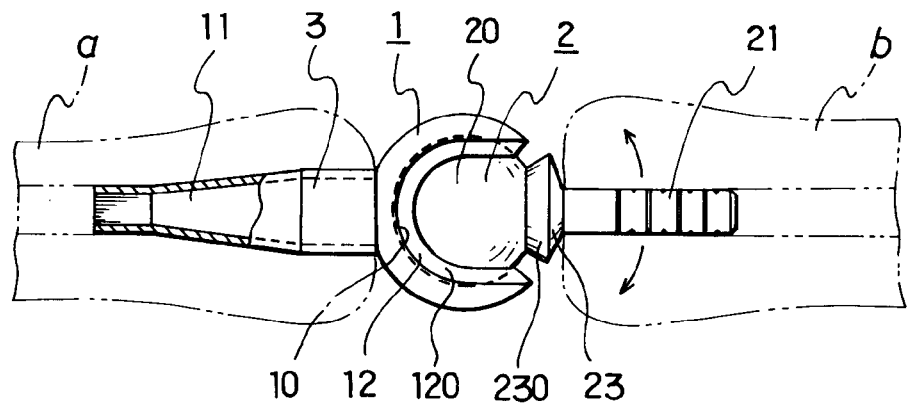
Fig. 12-A
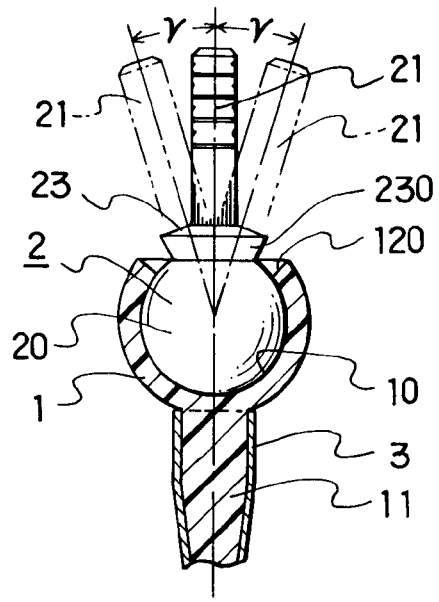
Fig. 12-B
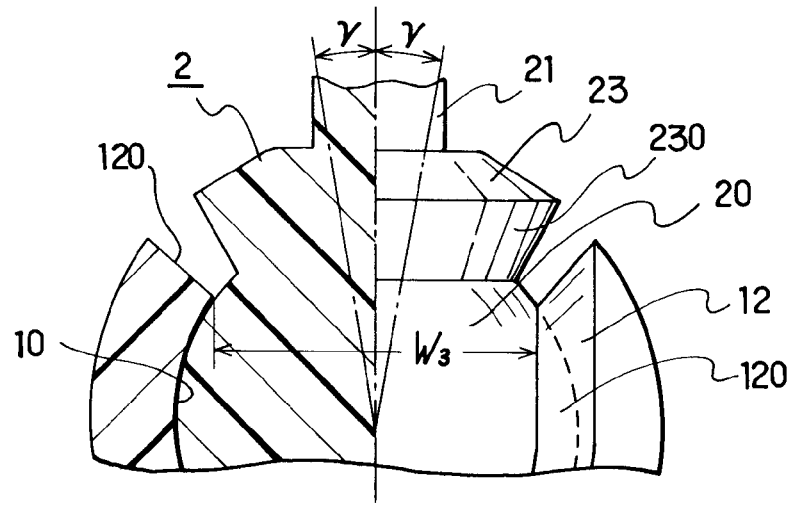

Fig. 13
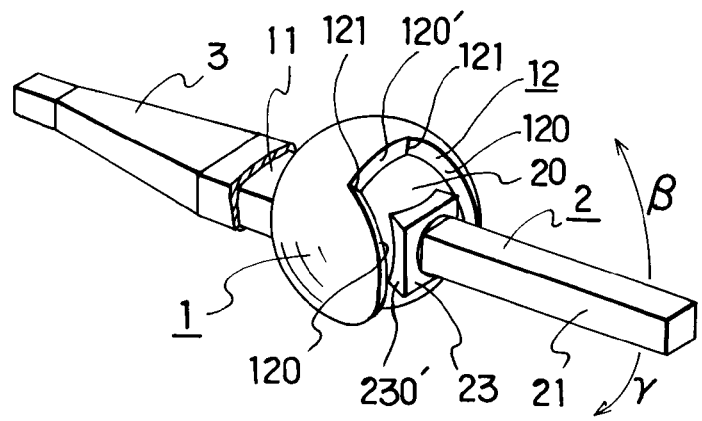
Fig. 14
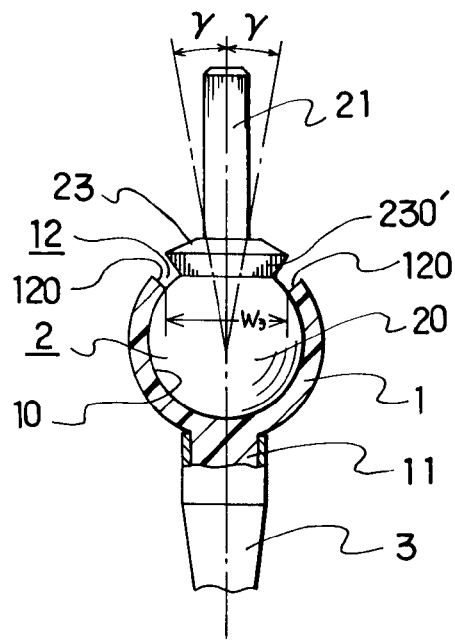
Fig. 15-A    Fig. 15-B    Fig. 15-C
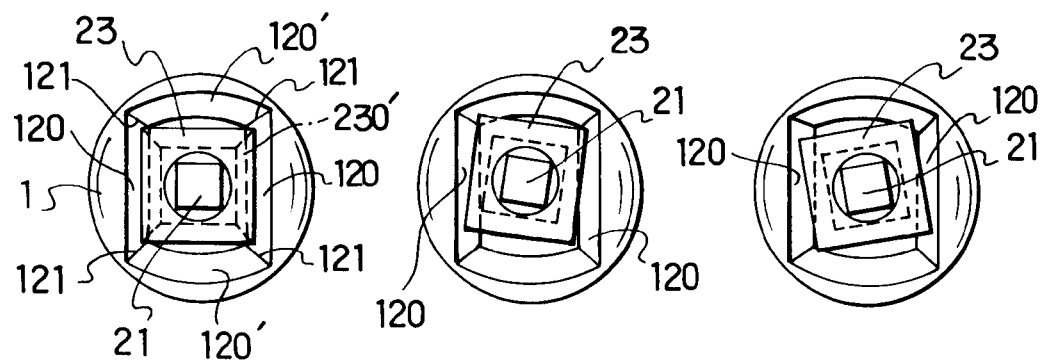

Fig. 18
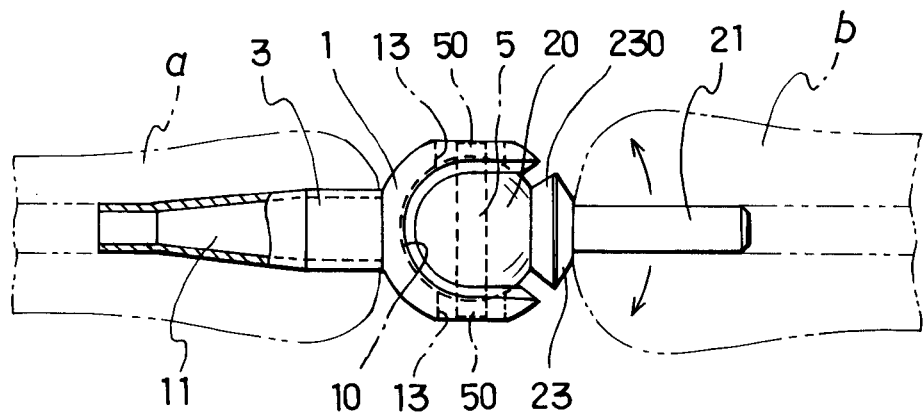
Fig. 19
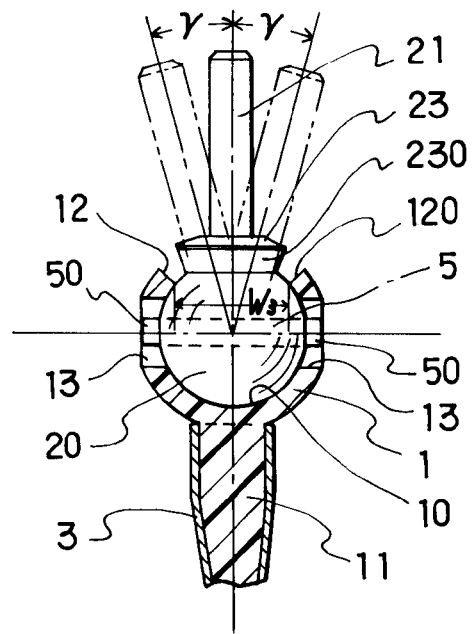
Fig. 20-A
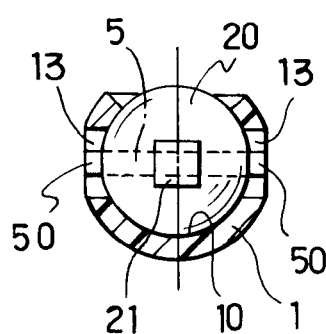
Fig. 20-B
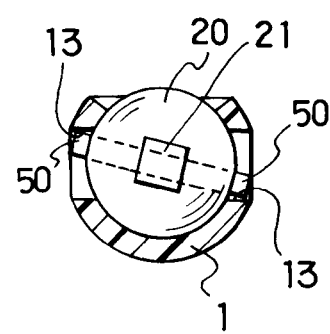
Fig. 20-C
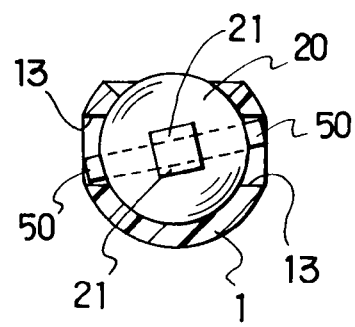

Fig. 23−A
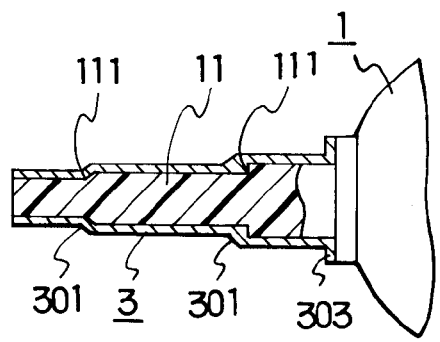
Fig. 23−B
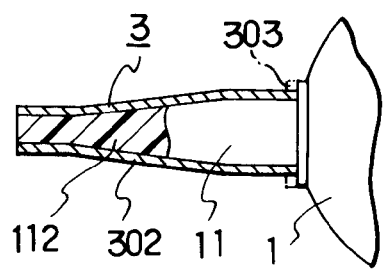
Fig. 23−C
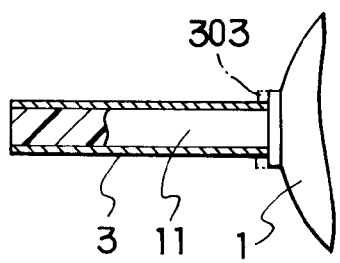
Fig. 23−D
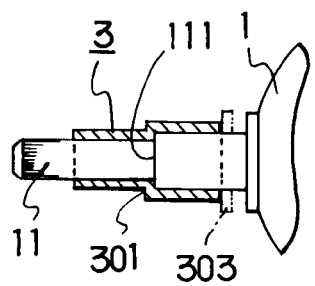
Fig. 23−E
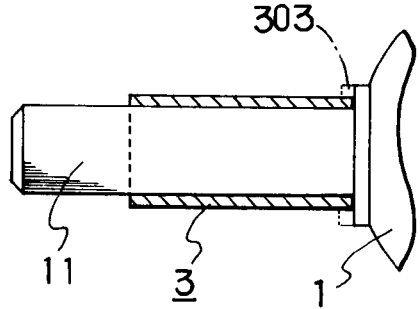

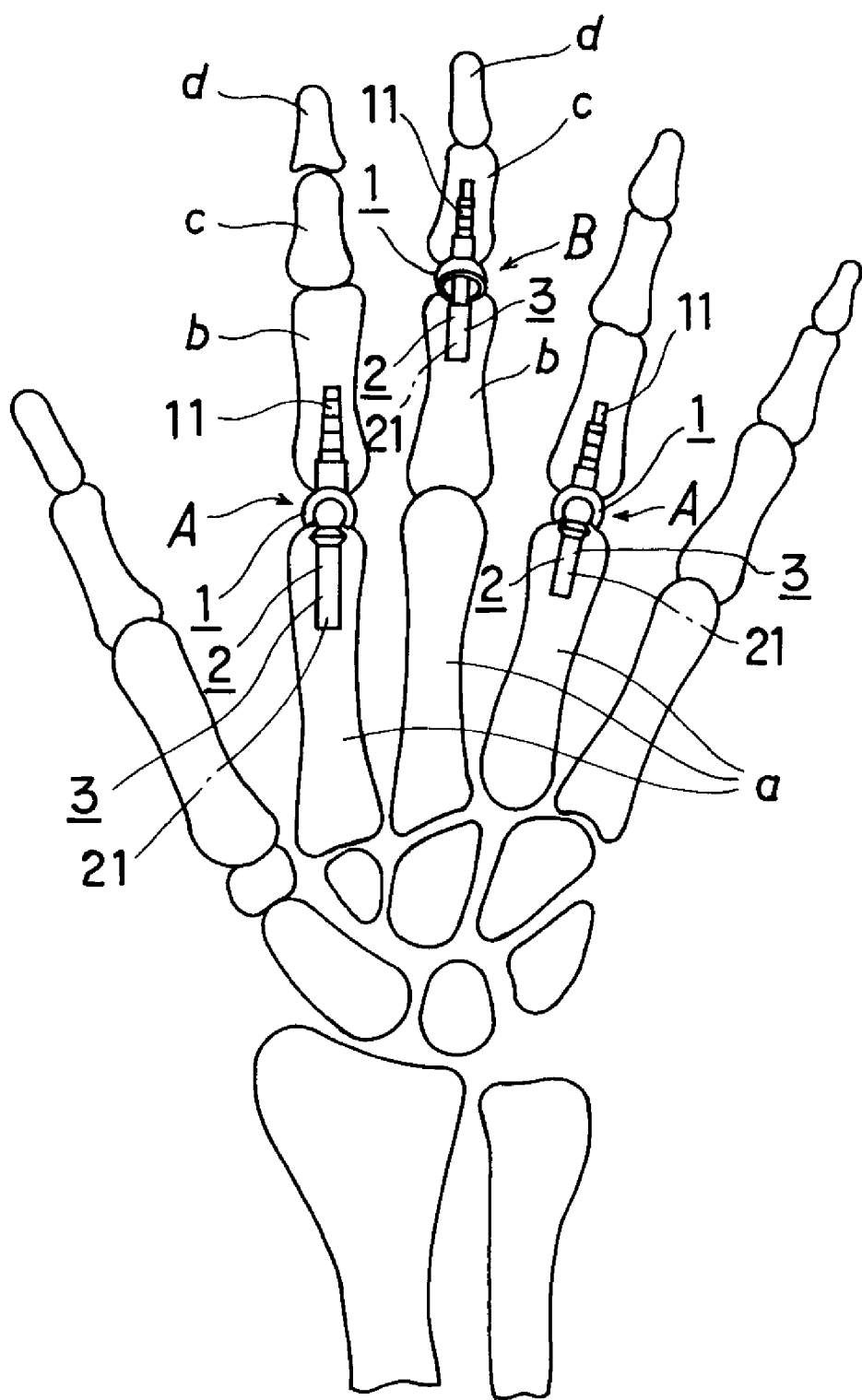
Fig. 25-A

Fig. 25-B
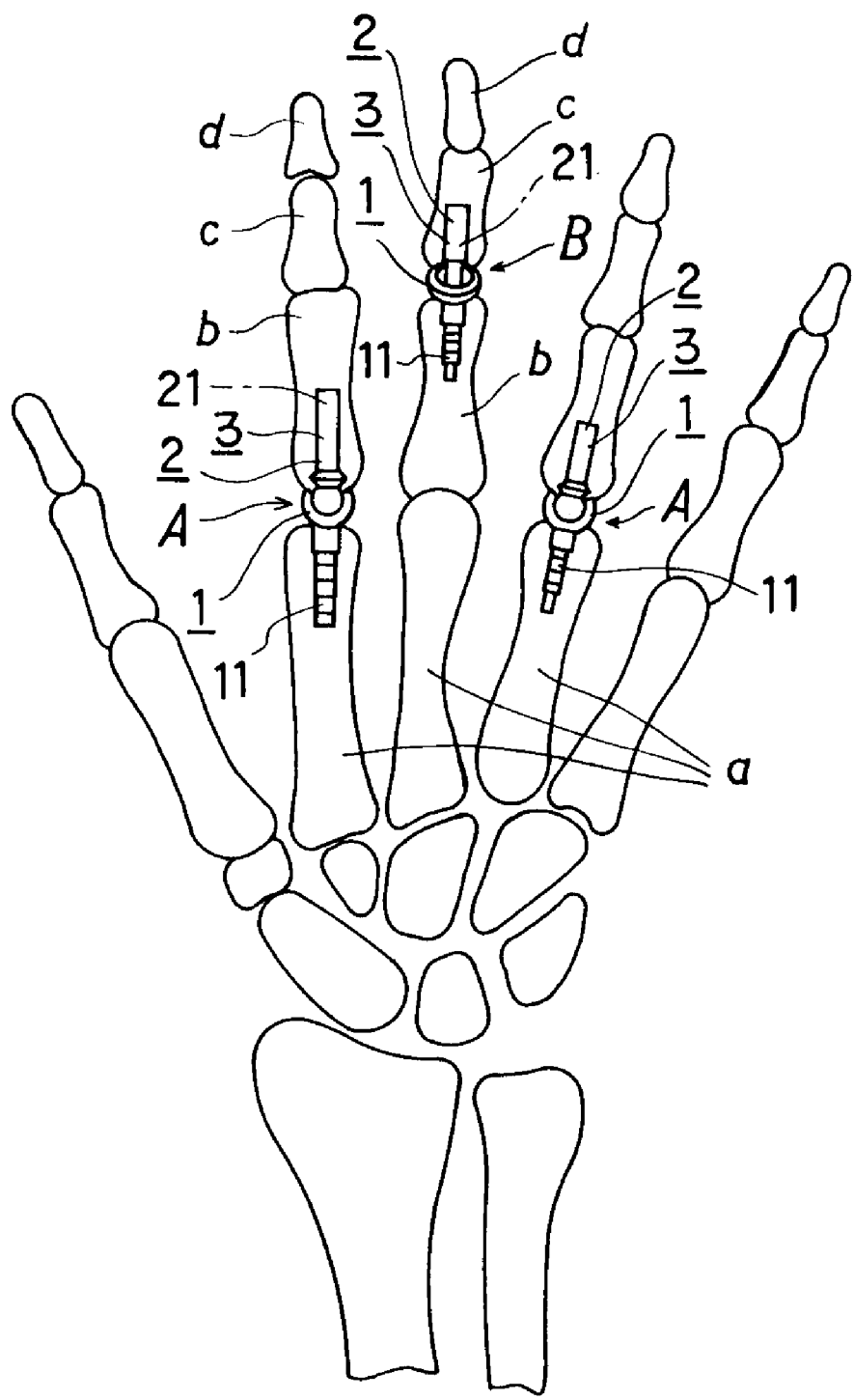

Fig. 28-A
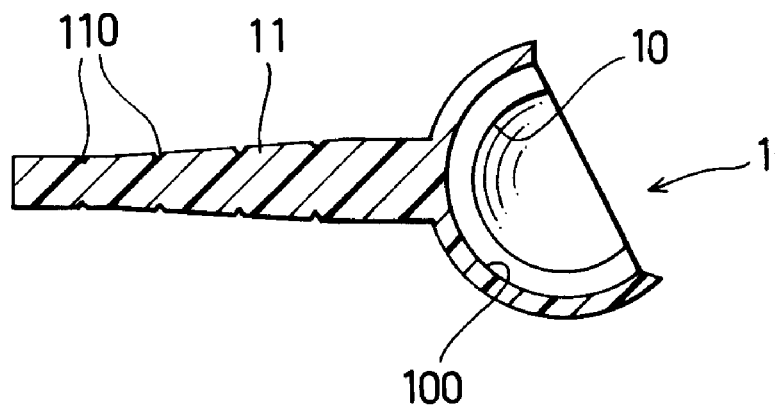
Fig. 28-B
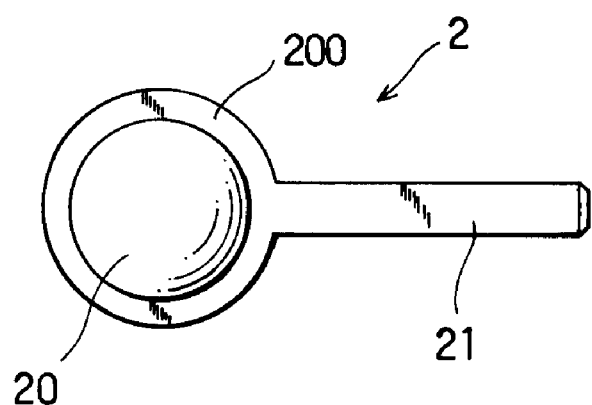
Fig. 28-C
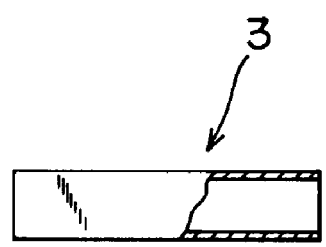

Fig. 33-A
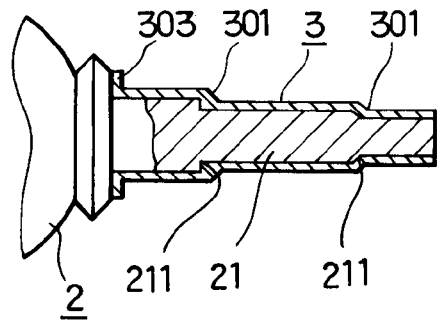
Fig. 33-B
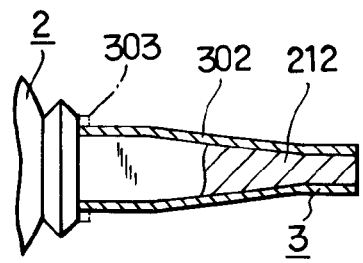
Fig. 33-C
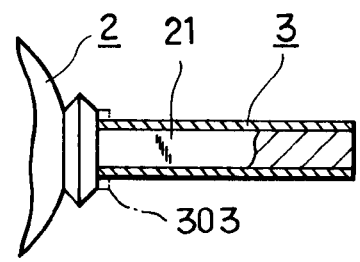
Fig. 33-D
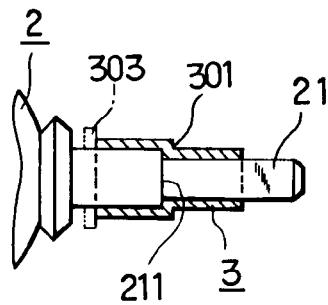
Fig. 33-E
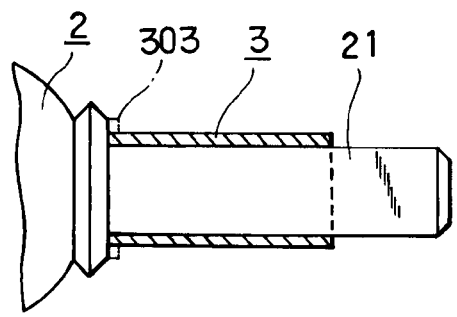

FINGER JOINT PROSTHESIS

This is a division of Application Ser. No. 09/015,032, filed on Jan. 28, 1998, now abandoned.

TECHNICAL FIELD

The present invention relates to a finger joint prosthesis, more particularly to a finger joint prosthesis preferable for being used for a metacarpophalangeal joint or a proximal interphalangeal joint or the like.

BACKGROUND ART

A metacarpophalangeal joint (hereinafter, referred to as MP joint) is constituted by a metacarpal bone and a proximal phalanx and a proximal interphalangeal joint (referred to as PIP joint) is constituted by a proximal phalanx and a middle phalanx. When a patient suffers from arthritis represented by rheumatoid arthritis, these joints, ligaments and tendons are gradually affected and deformation with ache and significant limitation in motion are shown.

As a countermeasure therefor, an operation is carried out for replacing a joint portion deformed by arthritis by a finger joint prosthesis.

Conventionally, such a finger joint prosthesis is generally provided with a structure having a middle flange portion and a shaft portion projected from the flange portion as a base end in the axial direction by using an elastic polymer material represented by silicone. However, according to the structure, the material is excessively flexible and therefore, wear or break is liable to result and further, the structure is weak at twist and therefore, nonphysiologic side flail behavior or circumflexing is liable to result.

Although a finger joint prosthesis made of a metal using a hinge has been proposed as a countermeasure therefor, it is the actual state that a practical product has not been proposed yet since a movable range is limited or physiologic movement is not carried out.

SUMMARY OF THE INVENTION

It is an object of the present invention to provide a finger joint prosthesis which is well matched with the motional characteristic of the finger and is highly practical with a comparatively simple structure.

A finger joint prosthesis according to the present invention is not only preferable to a metacarpophalangeal joint (hereinafter, referred to as MP joint) and proximal interphalangeal joint (hereinafter, referred to as PIP joint) of hand or foot as well as applicable to a distal interphalangeal joint (DIP joint) and further is effective as a joint prosthesis for hand or elbow other than the finger joint.

In order to achieve the above-described object, the present invention is constituted as follows.

According to an aspect of the present invention, there is provided a finger joint prosthesis of a style where stems are embedded into tubular bones at a remotely disposed portion and a nearly disposed portion of a finger joint, said finger joint prosthesis comprising a socket having an opening at one portion thereof and a spherical face at an inner side thereof and integrally formed with a stem on a side opposed to the opening, a head having a spherical portion to be fitted to the spherical face and integrally formed with a stem extending outwardly from the opening, a sheath surrounding either of the stem of the socket and the stem of the head, and wherein the stem can be moved slidably in an axial direction by adhering and fixing the sheath to a narrow cavity at the nearly disposed portion or the remotely disposed portion.

As one embodiment of the present invention, the spherical face is provided with a groove reaching the opening in a direction in which the stem is to be flexed and the spherical portion of the head is formed with a projected streak fitted to the groove. In this case, when the width of the groove is made larger than the width of the projected streak thereby intentionally providing play (gap) therebetween, pertinent side flexing or circumflexing can be carried out and accordingly, it is preferable to an MP joint. When the play is not provided, it is preferable to a PIP joint restricting the side flexing.

As other embodiment, the socket is formed with an opening in a shape of a long hole and a spherical portion of the head is fitted via the opening. Further, a projected trapezoidal portion having a conical side wall face is provided at the spherical portion of the head and the stem is extended forwardly from the projected trapezoidal portion. The opening in a shape of a long hole is provided with an inclined face at its edge portion and the side flexing angle is restricted by bringing the conical side wall face into contact with the inclined face. When the conical side wall face is formed into a pyramidal shape, both of the side flexing angle and circumflexing angle can be restricted by a simple structure. Further, when the conical side wall face and the inclined face are brought into a distance relationship where they are brought into contact to each other or proximate to each other, the side flexing is hampered and therefore, a preferable PIP joint can be constituted.

Further, although the socket and the spherical portion of the head may simply be fitted to each other, a pin may be penetrated through the spherical portion to be orthogonal to the direction of inclination of the stem. Thereby, the spherical portion of the head can firmly be prevented from coming off. Also, when window holes sufficiently larger than the outer diameter of the pin are provided in the socket, the circumflexing can simultaneously be restricted.

The above-described sheath not only promotes the adhesive performance in respect of a bone but guarantees very small extension in the axial direction accompanied by double axes type flexing motion particular to a joint. In addition thereto, the surface pressure between the socket and the spherical portion in the flexing and extending motion is reduced and smooth flexing and extending motion can be carried out over a long period of time. Preferably, the sheath is made of a metal material excellent in wear resistance and corrosion resistance.

According to the present invention, not only the flexing and extending motion can be carried out by a comparatively simple structure but both of the side flexing and circumflexing motion can be carried out by the ball joint structure and further, since the sheath is embedded and adhered into a narrow cavity and the sheath on the side of the socket or the sheath on the side of the head is slidably fitted thereto in the axial direction, smooth escape is provided, excessive surface pressure is not applied between the socket and the head in the flexing and extending motion by which the flexing motion can be carried out smoothly. Further, wear or destruction can be prevented and accordingly, the motional function that is stable over a long period of time can be achieved.

When play is intentionally provided between the groove on the equator of the spherical face of the socket and the projected streak of the spherical portion of the head, pertinent side flexing and circumflexing within a constant limit can be carried out by the play and a joint suitable for an MP joint can be provided.

When a groove both ends of which communicate with the opening portion is provided on the equator of the spherical face and the projected streak having a width substantially in coincidence with the width of the groove is formed on the outer periphery of the spherical portion of the head, smooth and stable flexing and extending function can be achieved and further, the side flexing and the circumflexing can be hampered by the groove on the equator of the spherical face of the socket and the projected streak of the spherical portion of the head and accordingly, an excellent PIP joint can be provided.

When a conical side wall face is provided at the spherical portion of the head and the side flexing angle is restricted by bringing the conical side wall face in contact with widening inclined faces at edge portions of the opening of the socket, a simple and inexpensive structure can be constituted while having effective function as an MP joint.

When a pyramidal side wall face is provided at the spherical portion of the head and the side flexing angle is restricted by bringing the pyramidal side wall face in contact with a pair of inclined faces provided at an opening having a square contour on the side of the socket and the circumflexing angle is restricted by bringing corner portions of the pyramidal side wall face in contact with the pair of inclined faces, a simple and inexpensive structure can be constituted while having sufficient function as an MP finger joint prosthesis.

When a pin penetrating through the spherical portion of the head is provided and projected portions at both ends of the pin are loosely fitted to widow holes of the socket, even when violent pull is effected, the separation of the socket from the head can be prevented and further, an effect where the side flexing angle can be restricted to a constant angle further firmly and the circumflexing angle can be restricted constant by bringing the projected portions of the pin in contact with the window holes is achieved.

When the opening is constituted in a shape of a long hole having inclined faces, a pin is penetrated through the spherical portion of the head orthogonal to the axial line of the stem, holes for supporting the both end portions of the pin are provided to the socket, the stem is formed to the spherical portion of the head via a projected trapezoidal portion, a conical side wall face is provided at the projected trapezoidal portion and the conical side wall face and the inclined face are brought into a distance relationship where they are brought into the contact with each other or proximate to each other, the separation of the socket from the head can be prevented even with violent pull and the side flexing and the circumflexing can be prevented by the pin and the holes and accordingly, a PIP finger joint prosthesis having excellent function can be constituted.

When the head and the sheath are made of a metal material excellent in corrosion resistance and wear resistance represented by a titanium alloy or a cobalt chromium alloy and the socket is made of a polymer compound excellent in wear resistance represented by ultra high molecular weight polyethylene, a finger joint prosthesis having high durability can be constituted.

Although other features or advantages of the present invention will be clarified by a detailed description as follows, it is apparent that so far as basic feature of the present invention is provided, the present invention is not limited to constitutions shown by embodiments but a skilled person can carry out various changes and modifications without deviating from the scope of the present invention.

BRIEF EXPLANATION OF THE DRAWINGS

FIG. 1-A is a partially cut plane view showing an example of using a first embodiment of a finger joint prosthesis according to the present invention;

FIG. 1-B is a partially cut plane view showing other example of using the first embodiment of the finger joint prosthesis according to the present invention;

FIG. 2 is a perspective view showing a first example of the first embodiment of an MP joint according to the present invention;

FIG. 6 is a sectional view taken along an X—X line of FIG. 4;

FIG. 7-A is a sectional view of a socket according to the first example;

FIG. 7-B is a plane view of the socket according to the fist example;

FIG. 7-C is a partially cut plane view of a sheath according to the first example;

FIG. 11 is a plane view of the same;

FIG. 12-A is a sectional view taken along a Y—Y line of FIG. 10;

FIG. 12-B is a partially magnified view thereof;

FIG. 13 is a perspective view showing a third example of the first embodiment of an MP joint according to the present invention;

FIG. 14 is a partially cut sectional view of the third example of the same;

FIG. 15-A is a front view of the third embodiment of the same;

FIG. 15-B shows a state of restricting a circumflexing angle of the third embodiment of the same;

FIG. 15-C shows a state of restricting the circumflexing angle of the third embodiment of the same;

FIG. 18 is a plane view of the fourth example of the same;

FIG. 19 is a cross-sectional view of the fourth example of the same;

FIG. 20-A is a front view of the fourth example of the same;

FIG. 20-B shows a state of restricting a circumflexing angle of the fourth example;

FIG. 20-C shows a state of restricting the circumflexing angle of the fourth example;

FIG. 23-A is a sectional view showing an example of a stem and a sheath according to a first embodiment of the present invention;

FIG. 23-B is a sectional view showing an example of a stem and a sheath according to the first embodiment of the present invention;

FIG. 23-C is a sectional view showing an example of a stem and a sheath according to the first embodiment of the present invention;

FIG. 23-D is a sectional view showing an example of a stem and a sheath according to the first embodiment of the present invention;

FIG. 23-E is a sectional view showing an example of a stem and a sheath according to the first embodiment of the present invention;

FIG. 25-A is a partially cut plane view showing an example of using a second embodiment of a finger joint prosthesis according to the present invention;

FIG. 25-B is a partially cut plane view showing other example of using the second embodiment of a finger joint prosthesis according to the present invention;

FIG. 28-A is a sectional view of a socket according to the first example;

FIG. 28-B is a plane view of a head according to the first example;

FIG. 28-C is a partially cut plane view of a sheath according to the first example;

FIG. 33-A is a sectional view showing an example of a stem and a sheath according to a second embodiment of the present invention;

FIG. 33-B is a sectional view showing an example of a stem and a sheath according to the second embodiment of the present invention;

FIG. 33-C is a sectional view showing an example of a stem and a sheath according to the second embodiment of the present invention;

FIG. 33-D is a sectional view showing an example of a stem and a sheath according to the second embodiment of the present invention; and FIG. 33-E is a sectional view showing an example of a stem and a sheath according to the second embodiment of the present invention.

DETAILED DESCRIPTION OF THE PREFERRED EMBODIMENT

Figure 3:
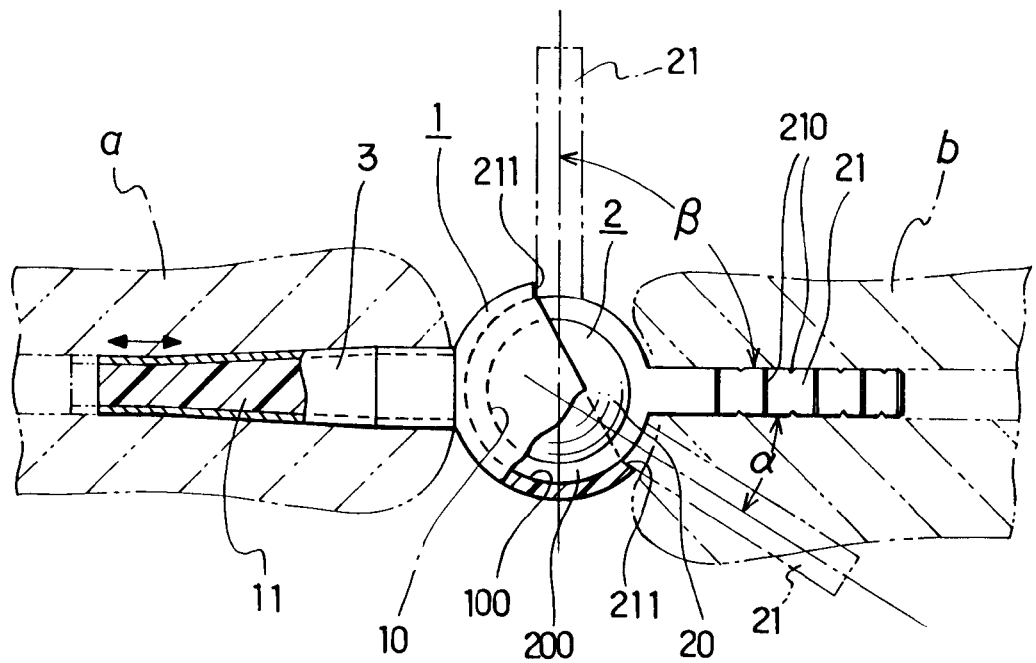
FIG. 3 is a partially cut side view showing a state of using the MP joint of FIG. 2.

An explanation will be given of embodiments of the present invention in reference to the attached drawings.

Embodiment 1

FIG. 1-A and FIG. 1-B show examples of a first embodiment to which a finger joint prosthesis according to the present invention is applied in which notation a designates a metacarpal bone, notation b designates a proximal phalanx, a notation c designates a middle phalanx and notation d designates a distal phalanx. Notation A designates an MP joint according to the present invention and notation B designates a PIP joint according to the present invention.

Each of the MP joint A and the PIP joint B is basically constituted by a socket 1, a head 2 and a sheath 3, the socket 1 is integrally provided with a stem 11, the head 2 is also integrally provided with a stem 21 and the sheath 3 is externally fitted to the stem 11 of the socket 1 movably relative to the stem 11.

The head 2 is made of a metal excellent in corrosion resistance, light weight formation and wear resistance, for example, a titanium series alloy or a cobalt chromium series alloy. Further, the sheath 3 is formed in a cylindrical shape also made of a metal excellent in corrosion resistance, light weight formation and wear resistance, for example, a titanium series alloy or a cobalt chromium series alloy. Although the socket 1 may be made of the above-described metals, preferably, it is made of a plastic excellent in wear resistance, for example, an engineering plastic represented by ultra high molecular weight polyethylene.

In the above-described MP joint A, the socket 1 is disposed at a gap portion between joint portions of the metacarpal bone a and the proximal phalanx b, that is, a gap portion provided by removing the joint portion of the metacarpal bone a or the joint portions of the metacarpal bone a and the proximal phalanx b. At the PIP joint B, the socket 1 is disposed at a gap portion between joint portions of the proximal phalanx b and the middle phalanx c, that is, a gap portion provided by removing the joint portion of the proximal phalanx b or the joint portions of the proximal phalanx b and the middle phalanx c.

Further, in the example of FIG. 1-A, according to the MP joint A, the sheath 3 is fixed to the metacarpal bone a and the stem 21 of the head 2 is fixed to the proximal phalanx b respectively by an adhesive agent such as bone cement. Further, in respect of the PIP joint B, the sheath 3 is fixed to the proximal phalanx b and the stem 21 of the head 2 is fixed to the middle phalanx c respectively by an adhesive agent such as bone cement.

In the example of FIG. 1-B, according to the MP joint A, the sheath 3 is fixed to the proximal phalanx b and the stem 21 of the head 2 is fixed to the metacarpal bone a respectively by an adhesive agent such as bone cement. Further, in respect of the PIP joint B, the sheath 3 is fixed to the middle phalanx c and the stem 21 of the head 2 is fixed to the proximal phalanx b respectively by an adhesive agent such as bone cement.

First Example of MP Joint A

FIG. 2 through FIG. 7-C show a first example of a first embodiment of an MP joint A according to the present invention.

The socket 1 is provided with a shape formed by cutting a spherical body the inside of which is hollow in a divided circular arc shape in view from a side face, for example, a shape produced by cutting a circle by a required angle of inclination in respect of a vertical line and a spherical face 10 is formed at inside of the socket 1.

The spherical face 10 is formed with a groove 100 having a required width $W_1$ at a portion in correspondence with a direction of flexing the stem (equator), mentioned later. The groove 100 is provided with a radius of curvature in correspondence with the spherical face 10 and both ends of the groove 100 in the longitudinal direction reach an opening 12 as the cut face.

Further, the stem 11 having a required length is integrally formed on the outer face of the socket 1 on an axial line the same as that of the groove 100 in the vertical face. It is preferable that at least two faces of the stem 11 are in parallel with each other in a section orthogonal to the axial line direction and in this example, the section forms substantially a quadrangle.

The head 2 is provided with a spherical portion 20 having an outer diameter slidably fitted to the spherical face 10.

A projected streak 200 in a band-like shape having a required width $W_2$ is formed integrally on the equator of the outer face of the spherical portion 20, the projected streak 200 is fitted to the groove 100 and is preferably brought into abrasive contact with the bottom of the groove.

Further, the stem 21 extending in the axial direction is formed integrally with the middle portion of the projected streak 200 in the peripheral direction. Although grooves 210 for fixing are formed on the stem 21 at pertinent intervals, the grooves 210 for fixing may not be provided when a case of drawing the stem 21 from a bone is considered.

It is necessary that the spherical face 10 of the socket 1 is provided with an area for surrounding a half or more of the spherical portion 20 and further, the opening 12 is set to an angle such that the stem 21 can be inclined by an arbitrary angle α within a range of 20° through 35° in the downward direction of the drawing in respect of the horizontal axial line and by an angle β of around 90° in the upward direction of the drawing as illustrated by FIG. 3 showing a state where the palm is directed upwardly.

Further, the width $W_2$ of the projected streak 200 is intentionally made narrower than the width $W_1$ of the groove 100 and is formed to a width of, for example, about a half through a third of the width $W_1$. Thereby, the stem 21 can be pivoted to the left and right by an amount of the difference ($W_1$–$W_2$) between the groove widths.

Although the length of the sheath 3 may be equal to or different from the length of the stem 11, it is preferable that the sheath 3 is provided with a sectional shape in conformity with a sectional shape of the stem 11.

Further, according to this example, the sectional area orthogonal to the longitudinal direction of the stem 11 is pertinently larger than that of the stem 21.

First Example of PIP Joint B

Figure 8:
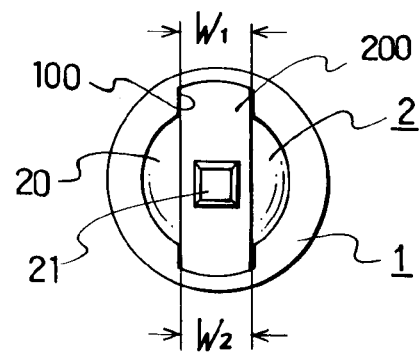
FIG. 8 is a front view showing the first example of a first embodiment of a PIP joint according to the present invention.
Figure 9:
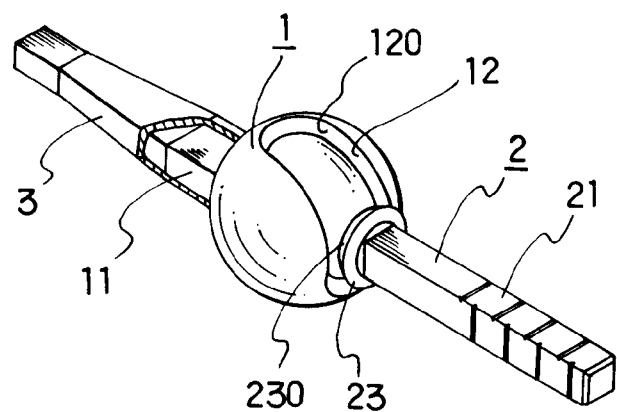
FIG. 9 is a perspective view showing a second example of the first embodiment of the MP joint according to the present invention.

FIG. 8 shows a first example of a PIP joint B according to the present invention.

Although the basic structure of the PIP joint B is similar to that of the above-described MP finger joint prosthesis A, a total thereof is formed in pertinently reduced dimensions. Further, according to the first example, the width $W_2$ of the projected streak 200 is provided with a dimension which is equivalent to or extremely approximated to the width $W_1$ of the groove 100 of the socket 1 by which the stem 21 is prevented from being pivoted in the left and right direction (prevented from side flexing).

The other constitution is the same as that of the MP finger joint prosthesis and therefore, the same notation is attached to the same portion and an explanation thereof will be omitted.

Second Example of MP Joint A

FIG. 9 through FIG. 12 show a second example of an MP joint A according to the present invention.

Also in this example, the MP joint A is provided with, as the basic structure, the socket 1 with a radius of curvature having the spherical face 10 at an inner side thereof, the head 2 having the spherical portion 20 and the stem 21, and the sheath 3 externally fitted slidably to the stem 11 integrally formed with the socket 1 and its material is similar to that of the above-described example.

Figure 10:
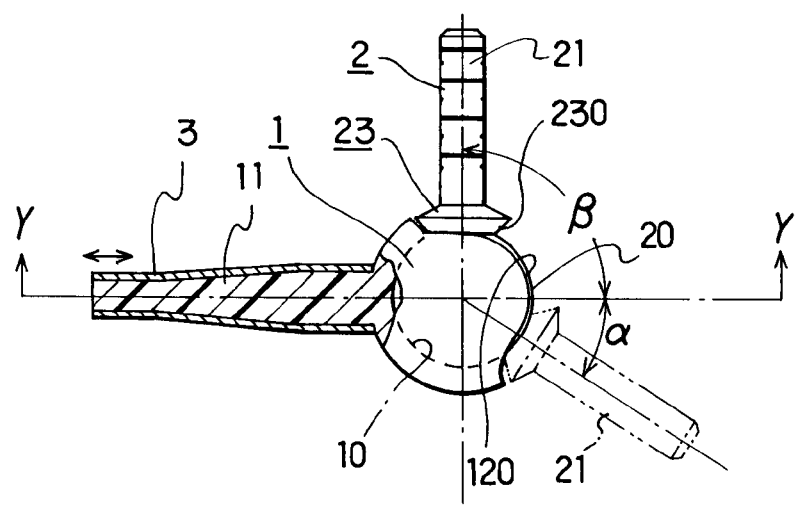
FIG. 10 is a partially cut side view of the same.
Figure 16:
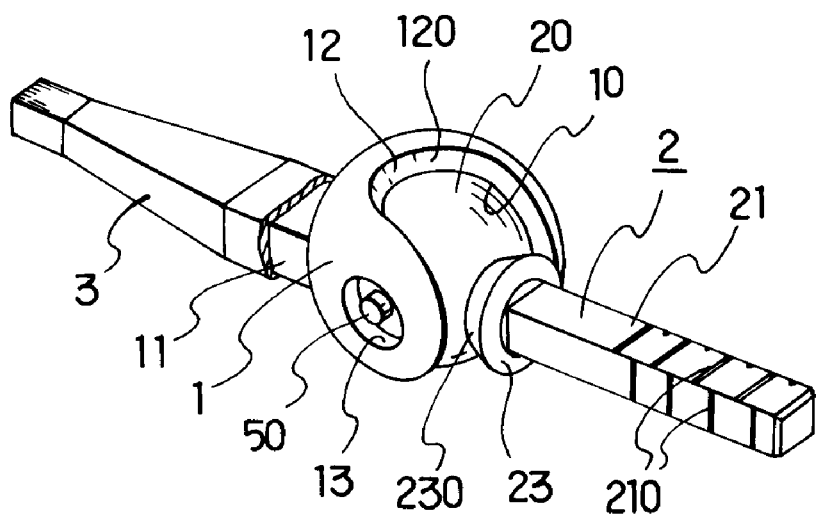
FIG. 16 is a perspective view showing a fourth example of the first embodiment of an MP joint according to the present invention.

However, according to the example, the socket 1 is provided with the opening 12 constituting a contour in a long hole shape or a shape similar to a long hole in view from a front face on the equator and the opening 12 is provided with lengths different from each other with the axial line of the stem 11 as a boundary to restrict the flexing angle as shown by FIG. 10. Further, the edge of the opening 12 is provided with an inclined face 120 widening outwardly by a required angle over the entire periphery as shown by FIG. 11, FIG. 12-A and FIG. 12-B.

Meanwhile, the head 2 is provided with the spherical portion 20 having the outer diameter slidably fitted to the spherical face 10, a projected trapezoidal portion 23 having a conical side wall face 230 is formed on the center line of the spherical portion 20 and the stem 21 is formed integrally with the projected trapezoidal portion 23 in front of the projected trapezoidal portion 23. The conical side wall face 230 of the projected trapezoidal portion 23 operates as a stopper in cooperation with the inclined face 120 of the opening 12 and a dimension of a root of the conical side wall face 230 is pertinently smaller than a width of the opening 12 (dimension $W_3$ between lower ends of the inclined face 120) as shown by FIG. 12-B. The projected trapezoidal portion 23 is circular in view from a front face.

Accordingly, as shown by FIG. 12-A and FIG. 12-B, the stem 21 can be pivoted (side flexing) in the left direction and in the right direction by an angle γ within a limit where the conical side wall face 230 is brought into contact with left and right sides of the inclined face 120. Further, as shown by FIG. 10, the stem 21 can be inclined by an arbitrary angle of α within a range of 20° through 350 in the downward direction of the drawing and by an angle β of around 90° in the upward direction of the drawing by bringing the conical side wall face 230 in contact with the upper and the lower ends of the inclined face 120.

The other structure is similar to that of the first example of the MP finger joint prosthesis A and accordingly, the same portion is attached with the same notation and an explanation thereof will be omitted.

Incidentally, when the size of the conical side wall faces 230 is made substantially equivalent to the width of the opening 12, the stem 21 cannot be pivoted in the left and right direction and accordingly, this constitution can be used in the PIP joint.

Third Example of MP Finger Joint Prosthesis A

FIG. 13 through FIG. 15 show a third example of the MP finger joint prosthesis A.

Also in this example, as the basic structure, the socket 1 having the spherical face 10 at an inner face thereof, the head 2 having the spherical portion 20 and the stem 21 extended therefrom in the axial direction, and the sheath 3 externally fitted slidably to the stem 11 integrally formed with the socket 1 are provided similar to those of the above-described examples and the material is similar to those in the above-described examples.

Also in this example, the socket 1 is provided with the opening 12 on the equator and the opening 12 is provided with different lengths with the axial line of the stem 11 as a boundary as shown by FIG. 13 and FIG. 14.

However, according to the example, inclined faces widening outwardly do not show an elliptical shape in view from a front face but as shown by FIG. 13, the left and right pair of the inclined faces 120 are connected to the upper and bottom pair of the inclined faces 120' by edge lines 121 by which a substantially polygonal shape (quadrangle in this embodiment) is constituted in view from a front face.

Meanwhile, the head 2 is provided with the spherical portion 20 having the outer diameter slidably fitted to the spherical face 10 and the projected trapezoidal portion 23 constituting a pyramidal side wall face 230' at the base portion on the center line of the spherical portion 20 and the stem 21 is formed integrally with the projected trapezoidal portion 23 in front of the projected trapezoidal portion 23. The pyramidal side wall face 230' operates as a stopper in cooperation with the left and right inclined faces 120 of the opening 12 and is provided with a dimension pertinently smaller than the width of the opening 12 (dimension $W_3$ between the lower ends of left and right inclined faces 120).

Accordingly, as shown by FIG. 14, the stem 21 can be pivoted (side flexing) by the angle in the left and right direction within the limit where the pyramidal side wall face 230' is brought into contact with the left and right inclined faces 120. Further, when the stem 21 is circumflexed around the axial line of its own from a state shown by FIG. 15-A, the circumflexing more than a constant value is restricted by bringing two corners on a diagonal line of the pyramidal side wall face 230' into contact with the left and right inclined faces 120 as shown by FIG. 15-B and FIG. 15-C.

Naturally, the stem 21 can be flexed within the limit where the pyramidal side wall face 230' is brought into contact with the upper and lower ends of the inclined faces 120'. That is, the stem 21 can be inclined by an arbitrary angle α within the range of 20° through 35° in the downward direction of the drawing and by an angle β of around 90° in the upward direction of the drawing similar to the above-described examples.

Other structure is similar to that of the first example of the MP joint A and accordingly, the same portion is attached with the same notation and an explanation thereof will be omitted.

Further, when in this example, the size of the pyramidal side wall face 230' is set to a dimension substantially in conformity with the width of the opening 12, the stem 21 can be prevented from being flexing sideways and therefore, this constitution is applicable to the PIP joint. In this case, it is necessary to reduce the size of the opening 12 such that the stem 21 can be flexed with the limit of an axial line the same as the axial line of the stem 11 (such that stem 21 can be inclined by the angle β of around 90°).

Fourth Example of MP Joint A

FIG. 16 through FIG. 20-C show a fourth example of the MP joint A.

Also in this example, as the basic structure, the MP joint A is provided with the socket 1 having the spherical face 10 at an inner face thereof, the head 2 having the spherical portion 20 and the stem 21 extending therefrom in the axial direction and the sheath 3 externally fitted slidably to the stem 11 integrally formed with the socket 1 and the material is similar to those in the above described examples.

Also in this example, the socket 1 is provided with the opening 12 in a long hole shape on the equator in view from a front face and the edge portion of the opening 12 constitutes the inclined face 120 widening outwardly by a required angle over the entire periphery as shown by FIG. 18 and FIG. 19.

Meanwhile, the projected trapezoidal portion 23 having the conical side wall face 230 is formed at the base portion on the center line of the spherical portion 20 of the head 2 and the stem 21 is formed integrally with the projected trapezoidal portion 23 in front of the projected trapezoidal portion 23. The conical side wall face 230 of the projected trapezoidal portion 23 is provided with a dimension pertinently smaller than the width of the opening 12 (dimension $W_3$ between lower ends of inclined face 120).

Figure 17:
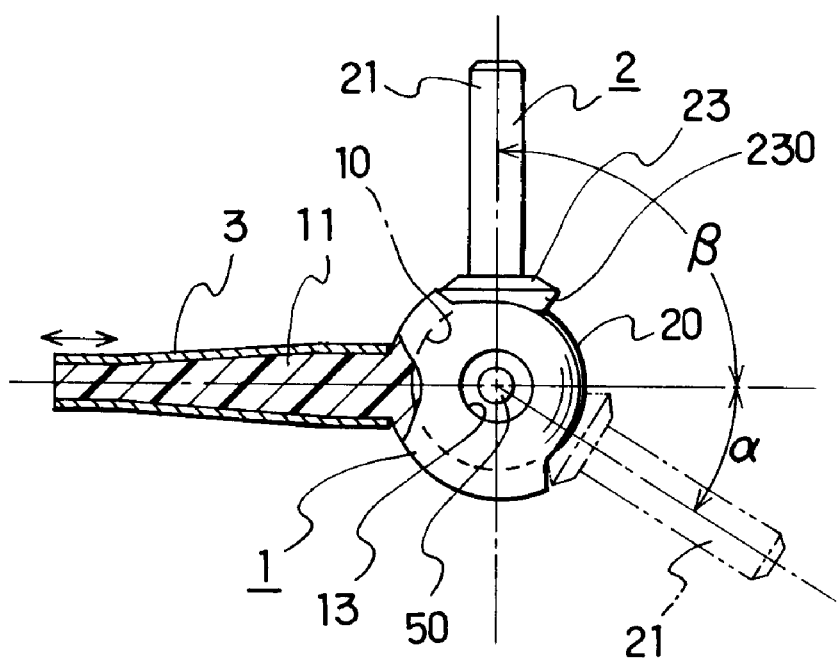
FIG. 17 is a partially cut side view of the fourth example of the same.

Although, such a constitution is the same as those of the second example and the third example, according to the fourth example, as shown by FIG. 17 through FIG. 19, a pin 5 penetrating through the center axis of the spherical portion 20 is attached to the spherical portion 20 of the head 2 as means for preventing detachment of ball and for restricting the circumflex angle and window holes 13 are formed in the socket l substantially concentric with both end portions 50 of the pin 5 projected from the spherical portion 20. The size of the window hole 13 is set in accordance with the circumflex angle to be restricted, for example, in a range of 1.5 through 2.5 time as large as the diameter of the pin 5.

The fourth example is provided with a function the same as those of the second and the third examples in respect of the flexing and extending and a function the same as those of the second and the third examples also in respect of the side flexing. However, according to the fourth example, the side flexing angle is restricted also by bringing the respective both end portions 50 of the pin 5 in contact with the window holes 13, that is, walls of the window holes. Therefore, the stability is further enhanced. Further, in respect of the circumflexing, when the stem 21 is circumflexed around the axial line of its own, by rotating the spherical portion 20, the both end portions 50 of the pin 5 are brought into contact with the upper and lower positions of the window holes 13 as shown by FIG. 20-B and FIG. 20-C and accordingly, the movement is restricted by a constant circumflex angle.

The other constitution is the same as those of the second example and the third example and therefore, a corresponding portion or part is attached with the 'same notation and an explanation thereof will be omitted.

Second Example of PIP Joint B

Figure 21:
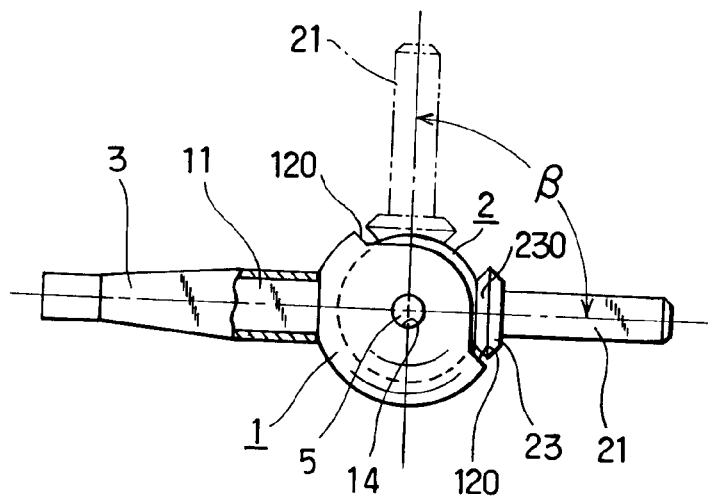
FIG. 21 is a partially cut side view showing a second example of the first embodiment of a PIP joint according to the present invention.
Figure 22:
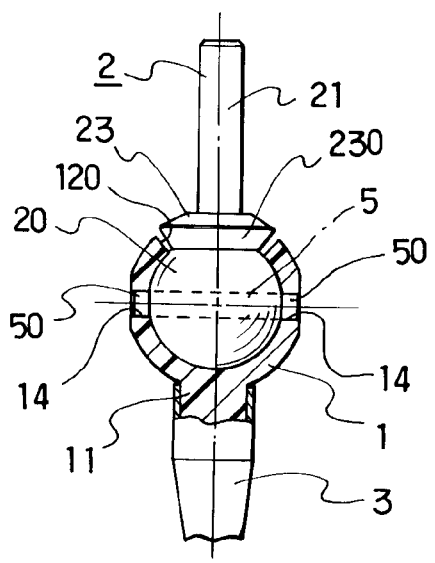
FIG. 22 is a partially cut plane view of the second example of the same.

FIG. 21 and FIG. 22 show a second example of a PIP joint B according to the present invention.

Although the basic constitution of the PIP joint B is the same as that of fourth example of the above-described MP joint A, instead of the window holes 13, holes 14 having a diameter substantially equal to that of the both end portions 50 of the pin 5 are constituted from the both sides of the socket 1. Further, the conical side wall face 230 of the projected trapezoidal portion 23 is provided with a dimension substantially equivalent to the width between the left and right sides of the inclined face 120 widening outwardly of the opening 12. The opening 12 is reduced such that the stem 12 can be flexed with a limit where the stem 12 is aligned with an axial line the same as the axial line of the stem 11.

Accordingly, although the second example is similar to the second example of the PIP joint B in respect of the flexing and extending, as shown by FIG. 22, the side flexing and circumflexing cannot be carried out owing to the contact between the conical side wall face 230 of the projected trapezoidal portion 23 and the inclined face 120 widening outwardly and the positional relationship between the pin 5 and the holes 14.

Common Item of First Embodiment

Further, FIG. 23-A through FIG. 23-E show respective embodiments of positional relationships between the sheath 3 and the stem 11 of the socket 1 in the above-described first embodiment of the present invention in which in FIG. 23-A through FIG. 23-C, the length of the sheath is made substantially equal to the length of the stem 11 of the socket 1 and in FIG. 23-D and FIG. 23-E, the length of the sheath is provided with a dimension shorter than the length of the stem 11 of the socket 1. Naturally, the length of the sheath may be longer than the length of the stem 11 of the socket 1.

In FIG. 23-A and FIG. 23-D, stepped portions 301 and 111 are provided at required positions of the sheath 3 and the stem 11 in the longitudinal direction by which the sectional area is reduced toward the free ends. In FIG. 23-B, the sectional area is reduced toward the front end by providing tapered portions 302 and 112. In FIG. 23-C and FIG. 23-E, the sheath 3 and the stem 11 are made straight.

In respect of the sheath 3 and the stem 11, it is preferable in view of preventing rotation that the section orthogonal to the axial line is noncircular over a total or at least more than a half of the entire length.

Depending on cases, the sheath 3 may be provided with a roughened surface or may be formed with irregularities by grooves or projected streaks in order to promote adhering performance with respect to bone cement.

Further, as exemplified in FIG. 23-A or as illustrated imaginarily in FIG. 23-B through FIG. 23-E, a flange 303 for a stopper may be provided at the base portion of the sheath 3. Thereby, when the sheath 3 is inserted and adhered to a narrow cavity of the metacarpal bone a or the proximal phalanx b, the sheath 3 can be prevented from sinking into the narrow cavity.

Incidentally, in respect of the stem 11 of the socket 1 and the stem 21 of the head 2, although in the illustrated examples, the sectional area of the stem 11 is larger than that of the stem 21, depending on cases, they may be equivalent to each other or the sectional area of the stem 11 may be smaller than that of the stem 21.

Figure 24:
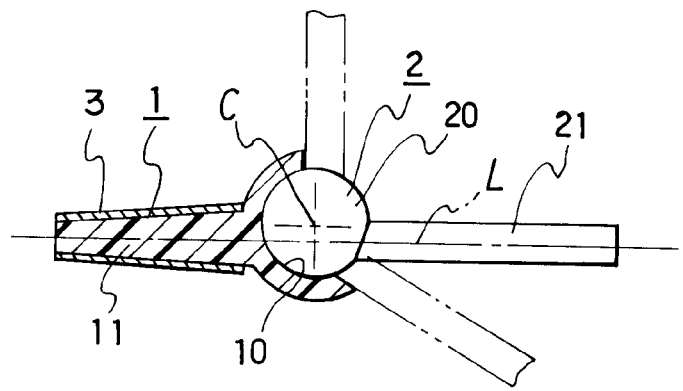
FIG. 24 is a side view showing other example of the first embodiment of the present invention.

Further, although in the above-described respective examples, the centers of the spherical portion 20 of the head 2 and the spherical face 10 of the socket 1 align with the axial lines of the stems 11 and 21, the present invention is not limited to these constitution. That is, as exemplified in FIG. 24, the center C of the spherical portion 20 of the head 2 and the spherical face 10 of the socket 1 may be deviated eccentric from the axial line L of the stems 11 and 21.

Embodiment 2

A second embodiment is featured in a positional relationship where the sheath 3 is fitted to the stem 21 of the head 2.

FIG. 25-A and FIG. 25-B show examples of using the second embodiment where notation a designates a metacarpal bone, notation b designates a proximal phalanx, a notation c designates a middle phalanx and notation d designates a distal phalanx. Notation A designates an MP joint according to the present invention and notation B designates a PIP joint according to the present invention.

Also in the second embodiment, each of the MP joint A and the PIP joint B is basically constituted by the socket 1, the head 2 and the sheath 3, the socket 1 is integrally provided with the stem 11 extending in the axial direction, the head 2 is also integrally provided with the stem 21 extending in the axial direction and the sheath 3 is externally fitted to the stem 21 of the head 2 movably relative to the stem 21.

In the MP joint A, the socket 1 is disposed at a gap portion between joint portions of the metacarpal bone a and the proximal phalanx b, and in the PIP joint B, it is disposed at a gap portion between joint portions of the proximal phalanx b and the middle phalanx c.

Further, according to the example of FIG. 25-A, the sheath 3 of the MP joint A is fixed to the metacarpal bone a and the stem 11 of the socket 1 is fixed to the proximal phalanx b respectively by an adhesive agent such as bone cement. Further, in respect of the PIP joint B, the sheath 3 is fixed to the proximal phalanx b and the stem 11 of the socket 1 is fixed to the middle phalanx c respectively by an adhesive agent such as bone cement.

According to the example of FIG. 25-B, the sheath 3 of the MP joint A is fixed to the proximal phalanx b and the stem 11 of the socket 1 is fixed to the metacarpal bone a respectively by an adhesive agent such as bone cement. Further, also in respect of the PIP joint B, the sheath 3 is fixed to the middle phalanx c and the stem 11 of the socket 1 is fixed to the proximal phalanx b respectively by an adhesive agent such as bone cement.

The materials or the like of the socket 1 and the head 2 are the same as those in the first embodiment.

First Example of MP Joint A

Figure 26:
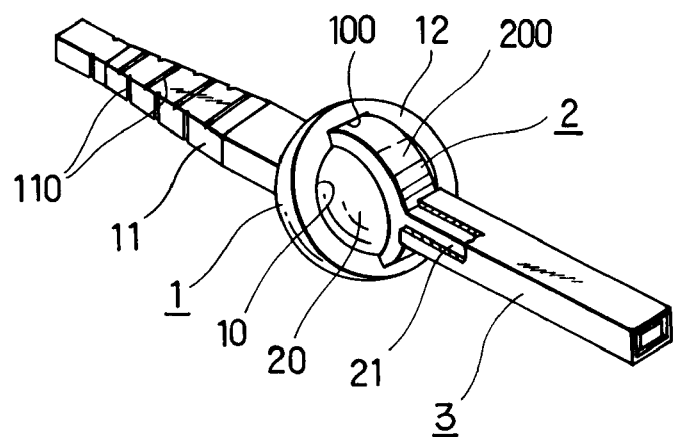
FIG. 26 is a perspective view showing a first example of a second embodiment of an MP joint according to the present invention.
Figure 27:
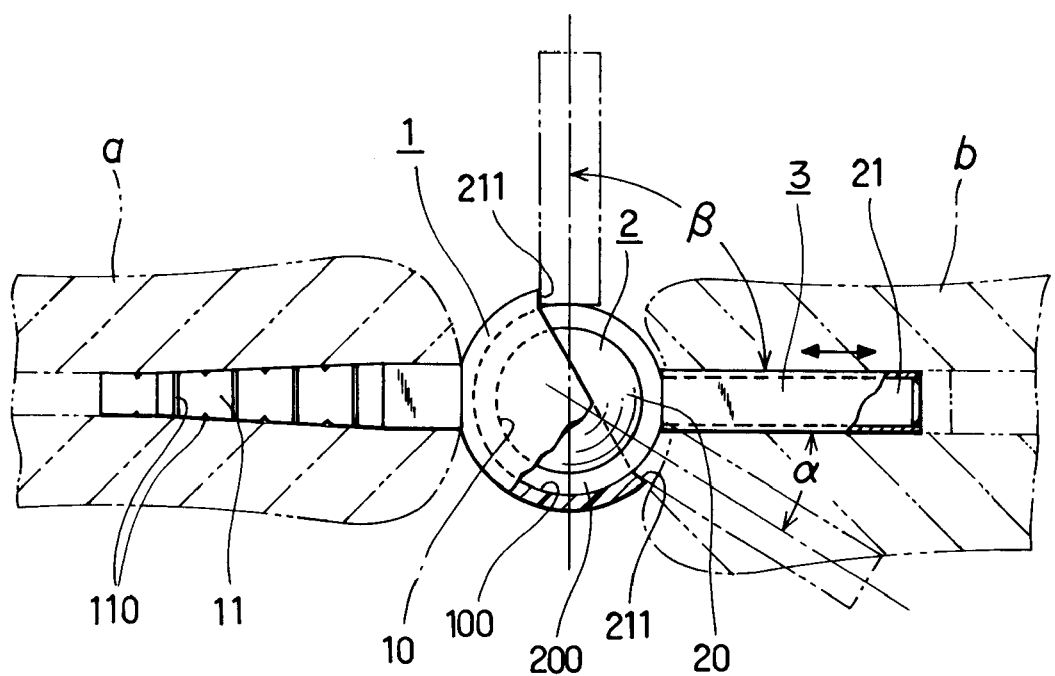
FIG. 27 is a partially cut side view showing a state of using the first example.

FIG. 26 through FIG. 28-C show a first example of the MP joint A.

The stem 11 having a required length is integrally formed with the outer face of the socket 1 on an axial line the same as that of the groove 100 in the vertical face and fixing grooves 110 are formed on the stem 11 at pertinent intervals. However, when a case where the stem 11 is drawn from a bone is considered, the fixing grooves 110 may not be provided.

The head 2 is provided with the spherical portion 20 having an outer diameter slidably fitted to the spherical face 10.

The projected streak 200 in a band-like shape having a required width $W_2$ is integrally formed with the spherical portion 20 on the equator at the outer face of the spherical portion 20 and the stem 21 extending in the axial direction is integrally formed with the middle portion of the projected streak 200 in the peripheral direction. The length of the sheath 3 fitted to the external side of the stem 21 slidably relative to the stem 21 may be the same as or different from the length of the stem 21, the sheath 3 is provided with the sectional shape in conformity with the sectional shape of the stem 21.

The other constitution is the same as the first example of the first embodiment and therefore, the same portion is attached with the same notation and an explanation thereof will be omitted.

Second Example of MP Joint A

Figure 29:
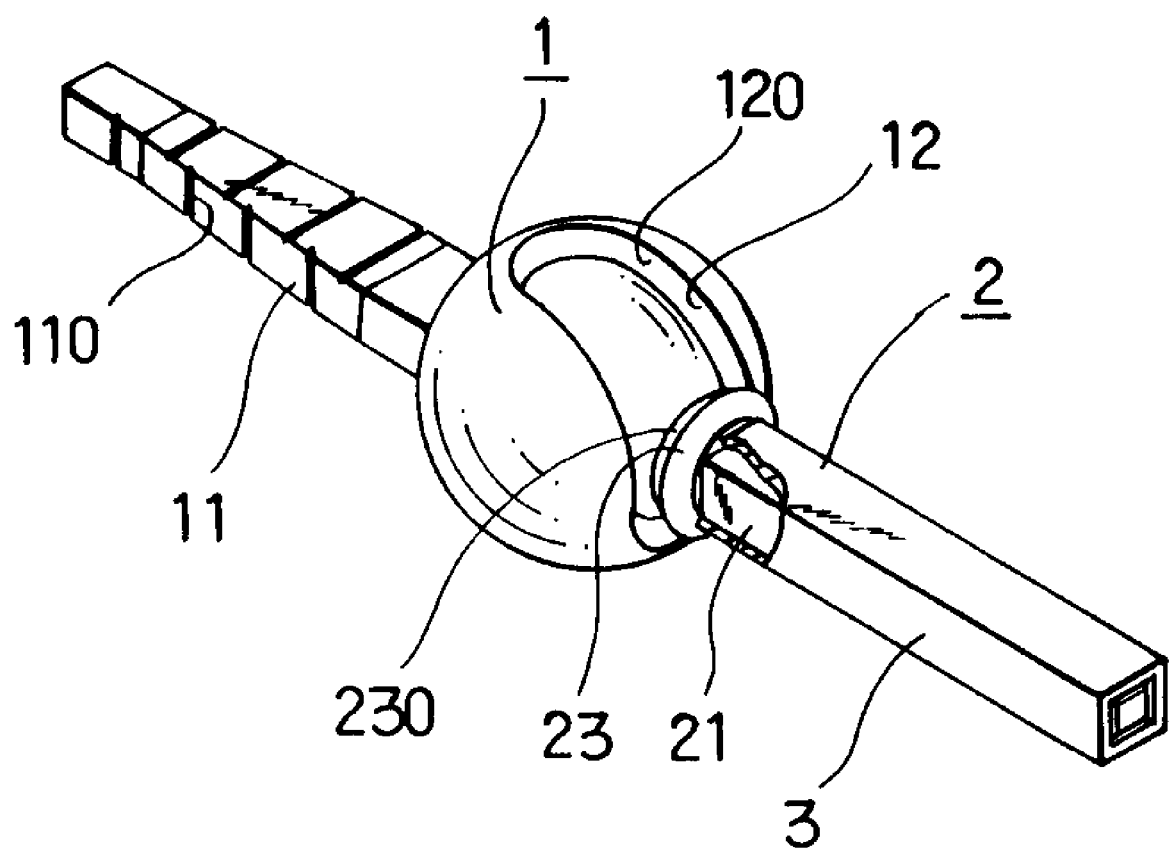
FIG. 29 is a perspective view showing a second example of the second embodiment of an MP joint according to the present invention.

FIG. 29 shows a second example of an MP joint A according to the present invention.

Also in this example, the MP joint A is provided with, as a basic structure, the stem 11 extending in the axial direction on the outer side, the socket 1 with a radius of curvature having the spherical face 10 on the inner side, the head 2 having the spherical portion 20 and the stem 21 extending therefrom in the axial direction and the sheath 3 and the material is the same as those of the above-described examples.

The projected trapezoidal portion 23 having the conical side wall face 230 is formed on the center line of the spherical portion 20 and the stem 21 is integrally formed with the projected trapezoidal portion .23 in front of the projected trapezoidal portion 23. The sheath 3 is externally fitted slidably to the stem 21 of the head 2.

The other constitution is the same as that of the second example according to the first embodiment of the MP finger joint prosthesis A and accordingly, the same portion is attached with the same notation and an explanation thereof will be omitted.

Third Example of MP Finger Joint Prosthesis A

Figure 30:
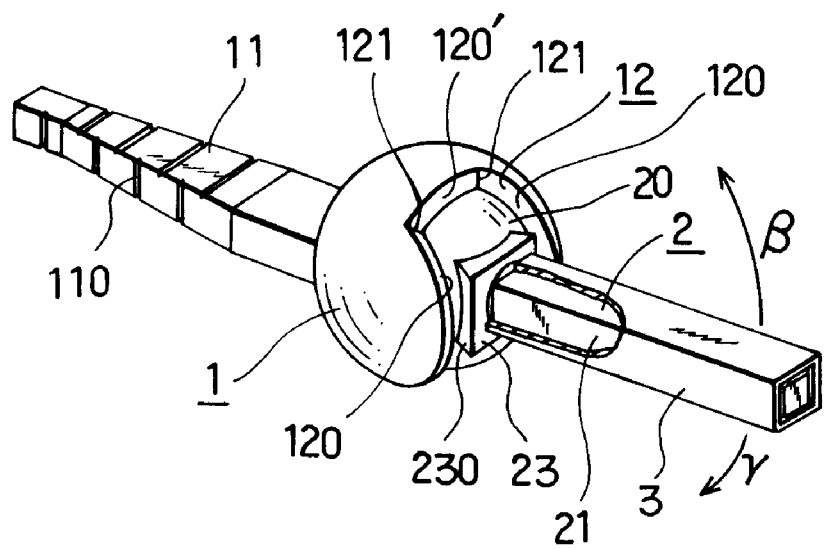
FIG. 30 is a perspective view showing a third example of the second embodiment of an MP joint according to the present invention.

FIG. 30 shows a third example of an MP finger joint prosthesis A.

Also this example is provided with the stem 11 on the outer side, the socket 1 having the spherical face 10 at the inner face, the head 2 having the spherical portion 20 and the stem 21 and the sheath 3 similar to the above-described examples and the material is similar to those in the above-described examples.

The projected trapezoidal portion 23 with the base portion constituting the pyramidal side wall face 230' is provided on the center line of the spherical portion 20, the stem .21 is integrally formed with the projected trapezoidal portion 23 in front of the projected trapezoidal portion 23 and the sheath 3 is externally fitted slidably to the stem 21.

The other structure is the same as that of the third example according to the first embodiment of the MP joint A and accordingly, the same portion is attached with the same notation and an explanation thereof will be omitted.

Fourth Example of MP Joint A

Figure 31:
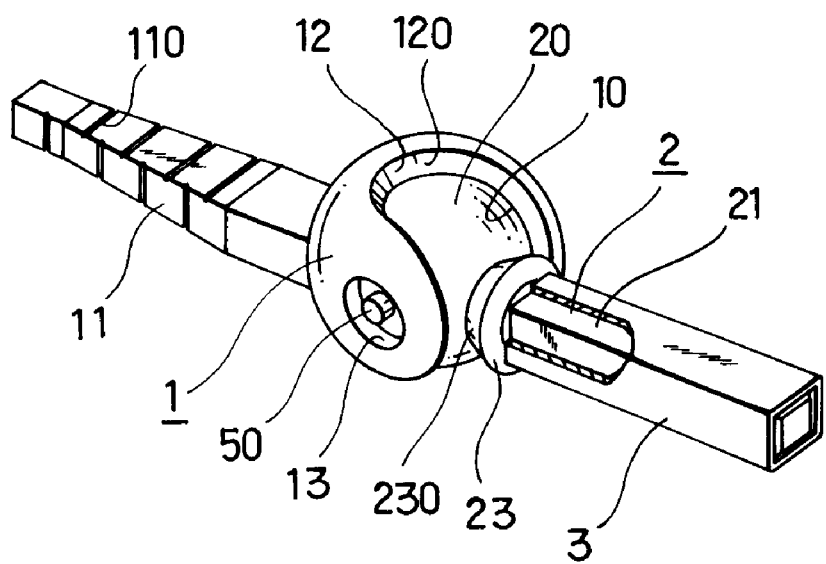
FIG. 31 is a perspective view showing a fourth example of the second embodiment of an MP joint according to the present invention.

FIG. 31 shows a fourth example of an MP joint A according to the present invention.

Also this example is provided with, as the basic structure, the socket 1 having the spherical face 10 on the inner face, the head 2 having the spherical portion 20 and the stem. 21 extending therefrom in the axial direction and the sheath 3 externally fitted slidably to the stem 21 integrally formed with the head 2 and the material is similar to those in the above-described examples.

Further, the projected trapezoidal portion 23 having the conical side wall face 230 at its base portion is formed on the center line of the spherical portion 20 of the head 2 and the stem 21 is integrally formed with the projected trapezoidal portion 23 in front of the projected trapezoidal portion 23.

The other constitution is the same as that of the fourth example according to the first embodiment and accordingly, a corresponding portion or part is attached with the same notation- and an explanation thereof will be omitted.

Example of PIP Joint B.

Figure 32:
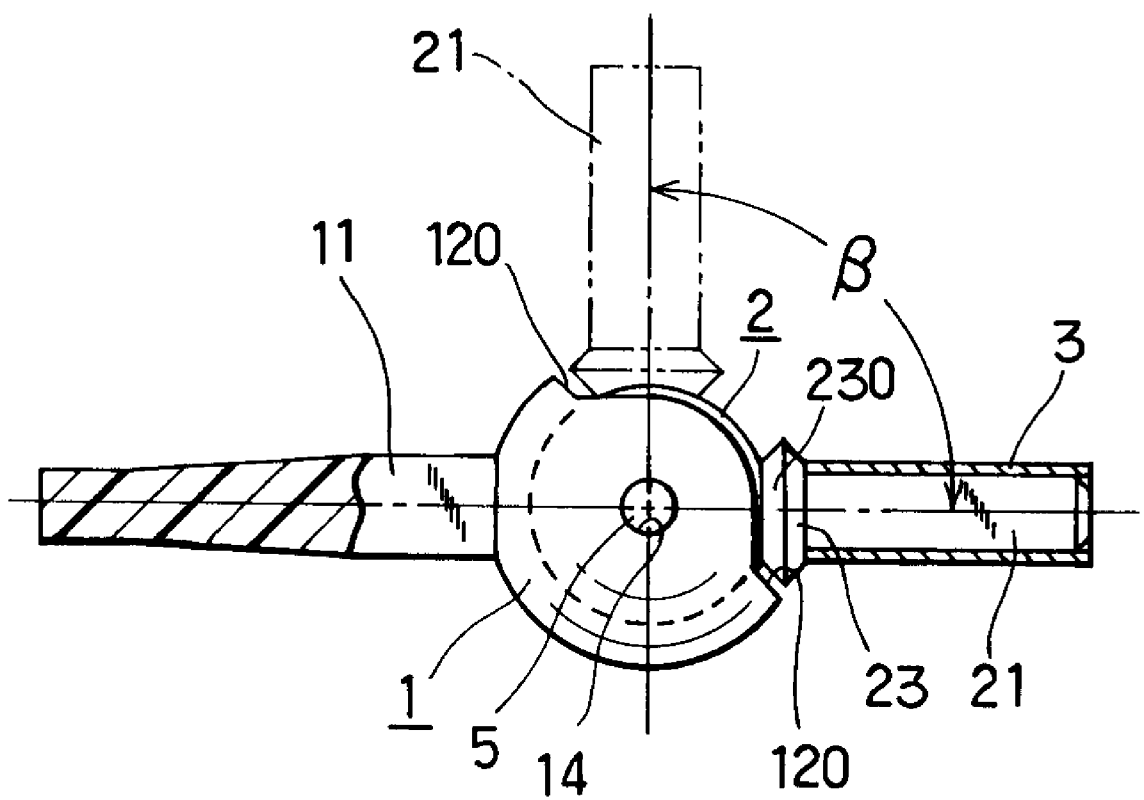
FIG. 32 is a partially cut side view showing an example of a second embodiment of a PIP joint according to the present invention.

FIG. 32 shows an example of a PIP joint B according to the present invention.

Also in the PIP joint B, the projected trapezoidal portion 23 having the conical side wall face 230 at its base portion is formed on the center line of the spherical portion 20 of the head 2, the stem 21 is integrally formed with the projected trapezoidal portion 23 in front of the projected trapezoidal portion 23 and the sheath 3 is externally fitted to the stem 21 slidably relative to the stem 21.

The other constitution is the same as that of the second example of the PIP joint B according to the first embodiment and accordingly, a corresponding portion or part is attached with the same notation and an explanation thereof will be omitted.

Common Item of Second Embodiment

Further, FIG. 33-A through FIG. 33-E show respective embodiments of positional relationships of the sheath 3 and the stem 21 of the head 2 according to the second embodiment of the present invention in which the length of the sheath is substantially the same as the length of the stem 21 of the head 2 in FIG. 33-A through FIG. 33-C, however, the length may be provided with a dimension shorter than that of the stem 21 of the head 2 as shown by FIG. 33-D and FIG. 33-E or may be conversely a dimension longer than that of the stem 21 of the,head 2.

In FIG. 33-A, the stepped portions 301 and 211 are provided at required positions of the sheath. 3 and the stem 21 in the longitudinal direction by which the sectional area is reduced toward the free end. In FIG. 33-B, the sectional area is reduced toward the front end by providing the tapered portions 302 and 212. In FIG. 23-C, the sheath 3 and the stem 21 are made straight.

OPERATION

Next, an explanation will be given of method of use and operation of the examples.

In respect of Embodiment 1

In replacing or reconstructing a joint by using the joint prosthesis of the present invention, in the case of the MP joint A, a joint portion of the metacarpal bone a or joint portions of the metacarpal bone a and the proximal phalanx b are removed. In the case of the PIP joint, a joint portion of the proximal phalanx b is removed or joint portions of the proximal phalanx b and the middle phalanx c are removed. Thereby, respective gap portions are formed and the socket 1 is positioned there.

Further, under this state the finger is flexed, according to the example of FIG. 1-A of the first embodiment, the sheath 3 is inserted into a narrow cavity of a bone on a nearly disposed side, that is, the metacarpal bone a in the case of the MP joint or a narrow cavity of the proximal phalanx b in the case of the PIP joint, respectively and the outer periphery of the sheath 3 is adhered and fixed to the narrow cavity by bone cement. Under the state, the stem 11 of the socket 1 is inserted into the sheath 3 and the stem 21 of the head 2 is inserted into a narrow cavity of a bone on a remotely disposed side, that is, the proximal phalanx b in the case of the MP joint or into a narrow cavity of the middle phalanx c in the case of the PIP joint and is adhered and fixed to the narrow cavity by bone cement.

In FIG. 1-B of the first embodiment, the sheath 3 is inserted into a narrow cavity of a bone on a remotely disposed side, that is, the proximal phalanx b in the case of the MP joint or a narrow cavity of the middle phalanx c in the case of the PIP joint, respectively and the outer periphery of the sheath 3 is adhered and fixed to the narrow cavity by bone cement. Under the state, the stem 11 of the socket 1 is inserted into the sheath 3 and the stem 21 of the head 2 is inserted into a narrow cavity of a bone on a nearly disposed side, that is, the metacarpal bone a in the case of the MP joint or a narrow cavity of the proximal phalanx b in the case of the PIP joint and is adhered and fixed to the narrow cavity by bone cement.

However, in either of FIG. 1-A and FIG. 1-B, depending on cases, the stem 21 of the head 2 may not be adhered and fixed to the narrow cavity but may be inserted into the narrow cavity. Further, depending on cases, the sheath 3 may be inserted into the narrow cavity in a state where the stem 11 is inserted into the sheath 3 and the outer periphery of the sheath 3 may be adhered and fixed to the narrow cavity by a bone cement.

In any cases, thereafter, ligaments or tendons are repaired. An explanation will be given of the operation of finger joint prosthesis provided as described above.

In Respect of the First Example of MP Joint A

According to the first example, the spherical portion 20 of the head 2 is brought into abrasive contact with the spherical face 10 of the socket 1 and therefore, flexing and overextending can be carried out as shown by imaginary lines of FIG. 3 within the limit where the root portion of the stem 21 of the head 2 is brought into contact with the upper and lower end portions 211 of the opening 12.

The finger joint of human being belongs to a rocking shaft type in view of the motion mechanism. Therefore, when the stem 21 of the head 2 and the stem 11 of the socket 1 are simply fixed to bones at a nearly disposed portion (remotely disposed portion) and a remotely disposed portion (nearly disposed portion), the head 2 and the socket 1 are compressed to each other in flexing and extending. Thereby, the surface pressure between the spherical portion 20 and the spherical face 10 becomes excessive, the flexing and extending cannot be carried out smoothly due to friction and there is a danger of wear or destruction of the spherical face 10 by repetition of shocking surface pressure.

However, according to the present invention, the stein 11 of the socket 1 is fitted movably to the sheath 3 in the axial direction relative to the sheath 3 that is adhered and fixed to the narrow cavity and therefore, in the above-described flexing and extending motion, the stem 11 is extracted and retracted to and from the sheath 3 naturally in accordance with the flexing angle by which the compressive load can be escaped. Therefore, the surface pressure between the spherical portion 20 and the spherical face 10 can be maintained low, the flexing and extending motion can be smoothly carried out, wear or destruction of the spherical face 10 can be prevented and the motional function that is stable over a long period of time can be maintained.

Figure 4:
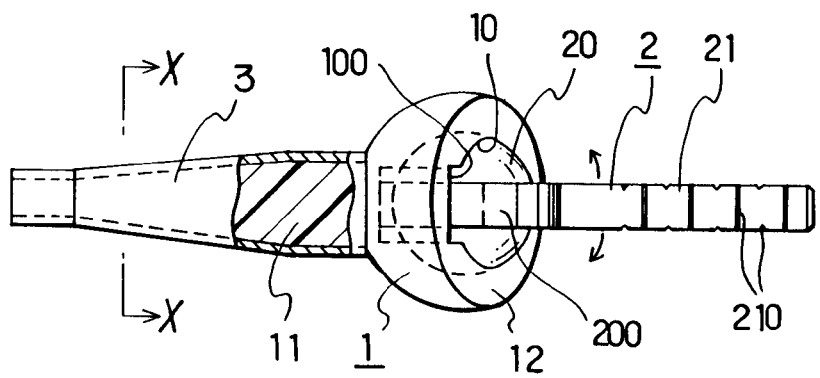
FIG. 4 is a partially cut plane view of the same.
Figure 5:
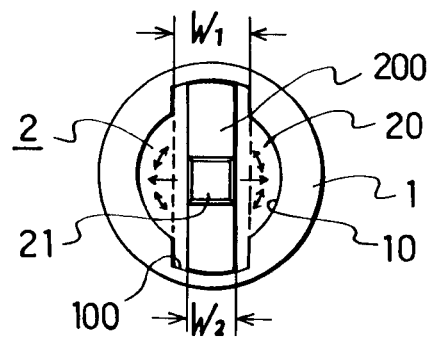
FIG. 5 is a front view of the same.

Further, the groove 100 is provided on the equator of the spherical face 10 of the socket 1 and the projected streak 200 having a width narrower than that of the groove 100 is provided to the spherical portion 20 of the head 2. Therefore, the stem 21 can be pivoted to the left and right within the limit where the side edges of the projected streak 200 are brought into contact with the side walls of the groove 100 as shown by FIG. 4 and accordingly, the side flexing motion of, for example, about 10° through 20° can be carried out. Further, the stem 21 can be circumflexed pertinently with the shaft line of its own as the center in view of the play relationship between the groove 100 and the projected streak 200.

Second Example of MP Joint A

According to the example, the flexing and extending motion can be carried out within the limit where the conical side wall face 230 of the projected trapezoidal portion 23 provided on the outer periphery of the spherical portion 20 can be moved along the opening 12 in an elliptical shape and is brought into contact with the inclined face 120. Further, also in this case, as mentioned above, the stem 11 of the socket 1 can be slidably moved relative to the sheath 3 and therefore, similar to the first example, the flexing and extending motion can be carried out smoothly.

Further, as shown by FIGS. 12-A and 12-B, the side flexing can be carried out within the limit where the conical side wall face 230 is brought into contact with the left and right sides of the inclined face 120.

Although in respect of the circumflexing motion, the movable range is not particularly restricted in this example, when ligaments, tendons and the like are secured, the circumflexing motion is restricted substantially thereby and accordingly, the MP joint A can be used.

In respect of Third Example of MP Joint A

According to the example, the stem 21 can smoothly carry out the flexing and extending motion similar to the second example within the limit where the pyramidal side wall face 230' is brought into contact with the pair of inclined faces 120' at the end portions. Further, as shown by FIG. 14, the stem 21 can realize the side flexing within the limit where the pyramidal side wall face 230' is brought into contact with the left and right pair of the inclined faces 120 and further, the circumflexing can be carried out within the limit where two corners on a diagonal line of the pyramidal side wall face 230' is brought into contact with the inclined faces 120 as shown by FIG. 15-A, FIG. 15-B and FIG. 15-C.

In respect of Fourth Example of MP Joint A

According to the example, the pin 5 is provided at the spherical portion 20 of the head 2 and the pin 5 is fitted to the window holes 13 of the socket 1 and therefore, even when the finger is pulled in the axial direction violently, the socket 1 and the head 2 are not separated from each other.

Further, the flexing and extending motion can be carried out smoothly similar to the second example. The side flexing can be carried out as shown by FIG. 19 within the limit where the conical side wall face 230 is brought into contact with the left and right sides of the inclined face 120 and as shown by FIG. 20-A through FIG. 20-C, the circumflexing can be carried out within the limit where the both end portions 50 of the pin 5 of the spherical portion 20 are brought into contact with the window holes 13 of the socket 1.

In respect of First Example of PIP Joint B

According to the first example of the PIP joint B shown by FIG. 8, the flexing and extending motion can be carried out freely and smoothly as mentioned above, however, the projected streak 200 provided at the spherical portion 20 of the head 2 is fitted tightly to the groove 100 of the socket 1 and therefore, the side flexing and the circumflexing are hampered.

In respect of Second Example of PIP Joint B

According to the second example of the PIP joint B shown by FIG. 21 and FIG. 22, although the flexing and extending motion can be carried out freely and smoothly as mentioned above, the side flexing cannot be carried out and the circumflexing is hampered since the conical side wall face 230 is brought into contact or nearly contact with the left and right sides of the inclined face 120 and the pin 5 of the spherical portion 20 of the head 2 is tightly fitted to the holes 14 of the socket 3.

Further, when the center C of the spherical portion 20 of the head 2 and the spherical face 10 of the socket 1 is made eccentric with the stems 11 and 21, the structure is in compliance with the actual state of the finger joint where much of nervous tissue or flesh is existed on the flexed side (on the palm side) and therefore, the flexing motion can be carried out smoothly.

In respect of Second Embodiment

Also in the second embodiment, in order to replace or reconstruct a joint, the gap portion is formed at joint portions of the metacarpal bone a and the proximal phalanx b in the case of the MP joint A and at joint portions of the proximal phalanx b and the middle phalanx c in the case. of the PIP joint, respectively and the socket 1 is disposed there.

Further, the finger is flexed in this state, and the sheath 3 is inserted into a bone on a nearly disposed side, that is, the metacarpal bone a in the case of the MP joint and the narrow cavity of the proximal phalanx b in the case of the PIP joint, respectively and the outer periphery of the sheath 3 is adhered and fixed to the narrow cavity by bone cement. Under this state, the stem 21 of the head 2 is inserted into the sheath 3 and the stem 11 of the socket 1 is inserted into the narrow cavity of a bone on a remotely disposed side, that is, the proximal phalanx b in the case of the MP joint or the narrow cavity of the middle phalanx c in the case of the PIP joint and is adhered and fixed to the narrow cavity by bone cement.

According to the example of FIG. 25-B, the sheath 3 is inserted into the narrow cavity of a bone on a remotely disposed side, that is, the proximal phalanx b in the case of the MP joint or the narrow cavity of the middle phalanx c in the case of the PIP joint, respectively and the outer periphery of the sheath 3 is adhered and fixed to the narrow cavity by bone cement. Under this state, the stem 21 of the head 2 is inserted into the sheath 3 and the stem 11 of the socket I is inserted into the narrow cavity of a bone on a nearly disposed side, that is, the metacarpal bone a in the case of the MP joint or the narrow cavity of the proximal phalanx b in the case of the PIP joint and is adhered and fixed to the narrow cavity by bone cement.

In either of FIG. 25-A and FIG. 25-B, depending on cases, the stem 11 of the socket 1 may not be adhered and fixed to the narrow cavity but may be simply inserted into the narrow cavity. Further, depending on cases, the sheath 3 may be inserted into the narrow cavity in a state where the stem 21 is inserted into the sheath 3 and the outer periphery of the sheath 3 may be adhered and fixed to the narrow cavity by bone cement.

The operation of the finger joint prosthesis provided as described above, is similar to that of the first embodiment except the following point. That is, the stem 21 of the head 2 is fitted to the sheath 3 adhered and fixed to the narrow cavity movably in the axial direction relative to the sheath 3 and therefore, in the flexing and extending motion, the stem 21 is extracted and retracted relative to the sheath 3 naturally in accordance with the flexing angle by which the compressive load can be escaped. Accordingly, the surface pressure between the spherical portion 20 and the spherical face 10 can be maintained low, the flexing and extending motion can be carried out smoothly and further, wear or destruction of the spherical face 10 can be prevented and the stable motional function can be maintained over a long period of time.

What is claimed is:

1. A finger joint prosthesis, comprising stems embeddable into tubular bones at a remotely disposed portion and a nearly disposed portion of a finger joint stems (11, 21); a socket (1) having an opening (12) at one portion and a spherical face (10) at an inner side and being integrally formed with one of the stems (11) on a side opposed to the opening (12); a head (2) having a spherical portion (20) to be fitted to the spherical face (10) and being integrally formed with the other of the stems (21) extending outwardly from the opening (10); a sheath (3) surrounding either of the stem (11) of the socket (1) and the stem (21) of the head (2), wherein at least half of a length of the sheath (3) and the stem (11, 21) orthogonal to an axial direction is non-circular, the stems (11, 21) being movable slideably in an axial direction by adhering and fixing the sheath (3) to a narrow cavity at the nearly disposed portion or the remotely disposed portion, the opening (12) being formed as a long hole having an inclined face (120) at an edge portion, the stem (21) of the head (20) having a projected trapezoidal portion (23) at a boundary between the stem (21) of the head (2) and the spherical portion (20), the projected trapezoidal portion (23) having a conical side wall face (230) at a side face and a side flexing angle is restricted by bringing the conical side wall face (230) into contact with the inclined face (120).

2. The finger joint prosthesis according to claim 1:
wherein the opening (12) has a four cornered shape having two pairs of inclined faces (120) and (120') at left, right, upper and lower sides thereof, the projected trapezoidal portion (23) has a pyramidal side wall face (230') at side faces thereof, a side flexing angle is restricted by bringing the pyramidal side wall face (230') in the contact with the pair of the inclined faces (120) and a circumflexing angle is restricted by bring corner portions of the pyramidal side wall face (230') in contact with the pair of inclined faces (120).

3. The finger joint prosthesis according to claim 2:
wherein the pyramidal side wall face (230') is in a relationship of being brought contact with the inclined faces (120) or proximate thereto by which a side flexing is restricted.

4. The finger joint prosthesis according to claim 1:
wherein the opening (12) has an inclined face (120'), a pin 5 is penetrated through the spherical portion (20) of the head (2) orthogonally to an axial line of the stem (21), window holes (13) for loosely fitting both end portions (50) of the pin (5) are installed to the socket (1), a side flexing angle is restricted by bringing the conical side wall face (230) in contact with the inclined face (120) and a circumflexing angle is restricted by bringing the both end portions (50) of the pin (5) in contact with the window hole (13).

5. The finger joint prosthesis according to claim 1:
wherein a pin 5 is penetrated through the spherical portion (20) of the head (2) orthogonally to an axial line of the stem (21), and the socket 1 has holes (14) for supporting both end portions (50) of the pin (5).

6. The finger joint prosthesis according to claim 1:
wherein the conical side wall face (230) is in a relationship of being brought into contact with the inclined face (120) or proximate thereto by which a side flexing is restricted.

7. The finger joint prosthesis according to claim 1:
wherein the spherical portion (20) of the head (2) is made eccentric with an axial line of the stem (11) of the socket (1).

8. The finger joint prosthesis according to claim 1:
wherein the head (2) and the sheath (3) are made of a metal material excellent in corrosion resistance and wear resistance represented by a titanium alloy or a cobalt chromium alloy and the socket (1) is made of a polymer compound excellent in wear resistance represented by ultra high molecular weight polyethylene.

9. The finger joint prosthesis according to claim 1:

wherein said finger joint prosthesis is applied to a metacarpophalangeal joint, the socket (1) is disposed at a gap portion between joint portions of a metacarpal bone (a) and a proximal phalanx (b), the sheath (3) is fixed to the metacarpal bone (a) and the stem (21) of the head (2) is fixed to the proximal phalanx (b) respectively by an adhesive agent.

10. The finger joint prosthesis according to claim 1:

wherein said finger joint prosthesis is applied to a metacarpophalangeal joint, the socket (1) is disposed at a gap portion between joint portions of a metacarpal bone (a) and a proximal phalanx (b), the sheath (3) is fixed to the proximal phalanx (b) and the stem (21) of the head (2) is fixed to the metacarpal bone (a) respectively by an adhesive agent.

11. The finger joint prosthesis according to claim 1:

wherein said finger joint prosthesis is applied to a metacarpophalangeal joint, the socket (1) is disposed at a gap portion between joint portions of a metacarpal bone (a) and a proximal phalanx (b), the sheath (3) is fixed to the metacarpal bone (a) and the stem (11) of the socket (1) is fixed to the proximal phalanx (b) respectively by an adhesive agent.

12. The finger joint prosthesis according to claim 1:

wherein said finger joint prosthesis is applied to a metacarpophalangeal joint, the socket (1) is disposed at a gap portion between joint portions of a metacarpal bone (a) and a proximal phalanx (b), the sheath (3) is fixed to the proximal phalanx (b) and the stem (11) of the socket (1) is fixed to the metacarpal bone (a) respectively by an adhesive agent.

13. The finger joint prosthesis according to claim 1:

wherein said finger joint prosthesis is applied to a proximal interphalangeal joint, the socket (1) is disposed at a gap portion between joint portions of a proximal phalanx (b) and a middle phalanx (c), the sheath (3) is fixed to the proximal phalanx (b) and the stem (21) of the head (2) is fixed to the middle phalanx (c) respectively by an adhesive agent.

14. The finger joint prosthesis according to claim 1:

wherein said finger joint prosthesis is applied to a proximal interphalangeal joint, the socket (1) is disposed at a gap portion between joint portions of a proximal phalanx (b) and a middle phalanx (c), the sheath (3) is fixed to the middle phalanx (c) and the stem (21) of the head (2) is fixed to the proximal phalanx (b) respectively by an adhesive agent.

15. The finger joint prosthesis according to claim 1:

wherein said finger joint prosthesis is applied to a proximal interphalangeal joint, the socket (1) is disposed at a gap portion between joint portions of a proximal phalanx (b) and a middle phalanx (c), the sheath (3) is fixed to the proximal phalanx (b) and the stem (11) of the socket (1) is fixed to the middle phalanx (c) respectively by an adhesive agent.

16. The finger joint prosthesis according to claim 1:

wherein said finger joint prosthesis is applied to a proximal interphalangeal joint, the socket (1) is disposed at a gap portion between joint portions of a proximal phalanx (b) and a middle phalanx (c), the sheath (3) is fixed to the middle phalanx (c) and the stem (11) of the socket (1) is fixed to the proximal phalanx (b) respectively by an adhesive agent.

* * * * *